(12) United States Patent
Furmanski et al.

(10) Patent No.: US 11,300,474 B2
(45) Date of Patent: *Apr. 12, 2022

(54) METHODS AND DEVICES FOR MONITORING THE INTEGRITY OF A FLUID CONNECTION

(71) Applicant: GAMBRO LUNDIA AB, Lund (SE)

(72) Inventors: Martin Furmanski, Malmo (SE); Anders Roslund, Malmo (SE); Bo Olde, Lund (SE); Kristian Solem, Kavlinge (SE); Thomas Hertz, Lund (SE); Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 325 days.

This patent is subject to a terminal disclaimer.

(21) Appl. No.: 15/240,421

(22) Filed: Aug. 18, 2016

(65) Prior Publication Data

US 2016/0356667 A1    Dec. 8, 2016

Related U.S. Application Data

(63) Continuation of application No. 13/001,314, filed as application No. PCT/EP2009/004640 on Jun. 26, 2009, now Pat. No. 9,442,036.

(Continued)

(30) Foreign Application Priority Data

Jun. 26, 2008 (SE) .................................. 0801517-4

(51) Int. Cl.
*G01M 3/28* (2006.01)
*A61M 1/36* (2006.01)
(Continued)

(52) U.S. Cl.
CPC ........ *G01M 3/2846* (2013.01); *A61M 1/3653* (2013.01); *A61M 1/3656* (2014.02);
(Continued)

(58) Field of Classification Search
None
See application file for complete search history.

(56) References Cited

U.S. PATENT DOCUMENTS 3,882,861 A    5/1975   Kettering et al.
3,946,731 A    3/1976   Lichtenstein
(Continued)

FOREIGN PATENT DOCUMENTS

CN    1913825    2/2007
DE    19609698   9/1997
(Continued)

OTHER PUBLICATIONS

Wabel et al., Ansätze zur Identifikation von Patientenparametern während der Hämodialysetherapie, Identification of Patient Parameters during Hemodialysis, vol. 50, Issue May 2002 (May 2002) pp. 220-227 ISSN (Print) 0178-2312, Published Online Sep. 25, 2009—English Translation—11 pages.

(Continued)

*Primary Examiner* — John C Kuan
(74) *Attorney, Agent, or Firm* — K&L Gates LLP

(57) ABSTRACT

A method of monitoring the integrity of a fluid connection between first and second fluid containing systems based on at least one time-dependent measurement signal from a pressure sensor in the first fluid containing system. The pressure sensor detects first pulses originating from a first pulse generator in the first fluid containing system and second pulses originating from a second pulse generator in the second fluid containing system. A parameter value representing a distribution of signal values within a time (Continued)

window is calculated by analyzing the measurement signal in the time domain and/or by using information on the timing of the second pulses in the measurement signal. The parameter value may be calculated as a statistical dispersion measure of the signal values, or from matching the signal to a predicted temporal signal profile of the second pulse. The integrity of the fluid connection is determined from the parameter value.

23 Claims, 13 Drawing Sheets

Related U.S. Application Data

(60) Provisional application No. 61/075,774, filed on Jun. 26, 2008.

(51) Int. Cl.
  *G01L 27/00* (2006.01)
  *G01N 33/49* (2006.01)

(52) U.S. Cl.
  CPC ........ *A61M 1/3659* (2014.02); *A61M 1/3661* (2014.02); *G01L 27/002* (2013.01); *G01M 3/2815* (2013.01); *G01N 33/49* (2013.01)

(56) References Cited

U.S. PATENT DOCUMENTS

| | | |
|---|---|---|
| 4,185,641 A | 1/1980 | Minior et al. |
| 4,239,047 A | 12/1980 | Griggs, III et al. |
| 4,277,227 A | 7/1981 | Jenkins |
| 4,353,368 A | 10/1982 | Slovak et al. |
| 4,392,847 A | 7/1983 | Whitney et al. |
| 4,450,527 A | 5/1984 | Sramek |
| 4,501,483 A | 2/1985 | Romansky et al. |
| 4,534,756 A | 8/1985 | Nelson |
| 4,541,282 A | 9/1985 | Auerweck et al. |
| 4,648,869 A | 3/1987 | Bobo, Jr. |
| 4,710,163 A | 12/1987 | Butterfield |
| 4,828,543 A | 5/1989 | Weiss et al. |
| 4,846,792 A | 7/1989 | Bobo, Jr. et al. |
| 4,923,598 A | 5/1990 | Schal |
| 4,959,050 A | 9/1990 | Bobo, Jr. |
| 4,972,826 A | 11/1990 | Koehler et al. |
| 4,979,940 A | 12/1990 | Bobo, Jr. et al. |
| 4,981,467 A | 1/1991 | Bobo, Jr. et al. |
| 5,026,348 A | 6/1991 | Venegas |
| 5,100,374 A | 3/1992 | Kageyama |
| 5,146,414 A | 9/1992 | McKown et al. |
| 5,311,871 A | 5/1994 | Yock |
| 5,427,695 A | 6/1995 | Brown |
| 5,557,263 A | 9/1996 | Fisher et al. |
| 5,693,008 A | 12/1997 | Brugger et al. |
| 5,790,036 A | 8/1998 | Fisher et al. |
| 5,830,365 A | 11/1998 | Schneditz |
| 5,863,421 A | 1/1999 | Peter, Jr. et al. |
| 5,906,589 A | 5/1999 | Gordon et al. |
| 5,910,252 A | 6/1999 | Truitt et al. |
| 6,066,261 A | 5/2000 | Spickermann |
| 6,071,421 A | 6/2000 | Brown |
| 6,077,443 A | 6/2000 | Goldau |
| 6,090,048 A | 7/2000 | Hertz et al. |
| 6,167,765 B1 | 1/2001 | Weitzel |
| 6,182,001 B1 | 1/2001 | Sugar et al. |
| 6,187,199 B1 | 2/2001 | Goldau |
| 6,200,485 B1 | 3/2001 | Kitaevich et al. |
| 6,221,040 B1 * | 4/2001 | Kleinekofort ........... A61M 1/16 604/4.01 |
| 6,258,027 B1 | 7/2001 | Sternby |
| 6,337,049 B1 | 1/2002 | Tamari |
| 6,470,258 B1 | 10/2002 | Leamy et al. |
| 6,501,344 B2 | 12/2002 | Ikata et al. |
| 6,572,576 B2 | 6/2003 | Brugger et al. |
| 6,575,927 B1 | 6/2003 | Weitzel et al. |
| 6,595,942 B2 | 7/2003 | Kleinekofort |
| 6,623,443 B1 | 9/2003 | Polaschegg |
| 6,649,063 B2 | 11/2003 | Brugger et al. |
| 6,663,585 B1 | 12/2003 | Ender |
| 6,695,806 B2 | 2/2004 | Gelfand et al. |
| 6,730,055 B2 | 5/2004 | Bainbridge et al. |
| 6,736,789 B1 | 5/2004 | Spickermann |
| 6,767,333 B1 | 7/2004 | Muller et al. |
| 6,773,670 B2 | 8/2004 | Stringer et al. |
| 6,780,159 B2 | 8/2004 | Sandler et al. |
| 6,804,991 B2 | 10/2004 | Balschat et al. |
| 6,827,698 B1 | 12/2004 | Kleinekofort |
| 6,880,404 B2 | 4/2005 | Uberreiter |
| 6,899,691 B2 | 5/2005 | Bainbridge et al. |
| 6,979,306 B2 | 12/2005 | Moll |
| 7,040,142 B2 | 5/2006 | Burbank |
| 7,060,047 B2 | 6/2006 | Lodi et al. |
| 7,087,033 B2 | 8/2006 | Brugger et al. |
| 7,169,352 B1 | 1/2007 | Felt et al. |
| 7,172,569 B2 | 2/2007 | Kleinekofort |
| 7,172,570 B2 | 2/2007 | Cavalcanti et al. |
| 7,276,041 B2 | 10/2007 | Moll |
| 7,410,473 B2 | 8/2008 | Levin et al. |
| 7,537,687 B2 | 5/2009 | Toyoda et al. |
| 7,575,562 B2 | 8/2009 | Oishi et al. |
| 7,597,666 B2 | 10/2009 | Frinak et al. |
| 7,615,028 B2 | 11/2009 | O'Mahony |
| 7,693,643 B2 | 4/2010 | Kim et al. |
| 7,771,380 B2 | 8/2010 | Jonsson et al. |
| 8,152,751 B2 | 4/2012 | Roger et al. |
| 8,197,421 B2 | 6/2012 | Freeman et al. |
| 8,197,431 B2 | 6/2012 | Bennison |
| 8,246,826 B2 | 8/2012 | Wilt et al. |
| 8,348,850 B2 | 1/2013 | Frinak et al. |
| 8,535,522 B2 | 9/2013 | Fulkerson et al. |
| 8,597,505 B2 | 12/2013 | Fulkerson et al. |
| 8,603,020 B2 | 12/2013 | Roger et al. |
| 8,608,658 B2 | 12/2013 | Burbank et al. |
| 8,641,615 B2 | 2/2014 | Burbank et al. |
| 2001/0007930 A1 | 7/2001 | Kleinekofort |
| 2002/0004636 A1 | 1/2002 | Tsubata |
| 2002/0198483 A1 | 12/2002 | Wariar et al. |
| 2003/0009123 A1 | 1/2003 | Brugger et al. |
| 2003/0128125 A1 | 7/2003 | Burbank et al. |
| 2003/0130607 A1 | 7/2003 | Delvano et al. |
| 2003/0152482 A1 | 8/2003 | O'Mahony et al. |
| 2004/0030277 A1 | 2/2004 | O'Mahony et al. |
| 2004/0041792 A1 | 3/2004 | Criscione |
| 2004/0171977 A1 | 9/2004 | Paolini et al. |
| 2004/0186409 A1 | 9/2004 | Cavalcanti et al. |
| 2004/0228760 A1 | 11/2004 | Stringer et al. |
| 2005/0004502 A1 | 1/2005 | O'Mahony et al. |
| 2005/0010118 A1 | 1/2005 | Toyoda et al. |
| 2005/0131332 A1 | 6/2005 | Kelly et al. |
| 2005/0230313 A1 | 10/2005 | O'Mahony et al. |
| 2006/0047193 A1 * | 3/2006 | Zhang .................... A61M 1/16 600/368 |
| 2006/0081517 A1 | 4/2006 | Toyoda et al. |
| 2006/0122552 A1 | 6/2006 | O'Mahony |
| 2006/0283652 A1 | 12/2006 | Yanai et al. |
| 2007/0004996 A1 | 1/2007 | Lovejoy et al. |
| 2007/0004997 A1 | 1/2007 | Felt et al. |
| 2007/0010779 A1 | 1/2007 | Utterberg et al. |
| 2007/0078368 A1 | 4/2007 | Felt et al. |
| 2007/0093774 A1 | 4/2007 | Felt et al. |
| 2007/0108128 A1 | 5/2007 | Koperschmidt et al. |
| 2007/0112289 A1 | 5/2007 | Cavalcanti et al. |
| 2007/0117010 A1 * | 5/2007 | Shang .................... A61M 1/16 429/163 |
| 2007/0179433 A1 | 8/2007 | Jonsson et al. |
| 2007/0232980 A1 | 10/2007 | Felt et al. |
| 2008/0004904 A1 | 1/2008 | Tran |
| 2008/0074307 A1 | 3/2008 | Boric-Lubecke et al. |
| 2008/0091118 A1 | 4/2008 | Georgopoulos |
| 2008/0108930 A1 | 5/2008 | Weitzel et al. |
| 2008/0171960 A1 | 7/2008 | Brieske et al. |
| 2008/0183120 A1 | 7/2008 | Utterberg et al. |

(56) References Cited

U.S. PATENT DOCUMENTS

| | | |
|---|---|---|
| 2008/0195022 A1 | 8/2008 | Lucke et al. |
| 2008/0214979 A1 | 9/2008 | Brugger et al. |
| 2008/0312542 A1 | 12/2008 | Banet et al. |
| 2009/0008331 A1 | 1/2009 | Wilt et al. |
| 2009/0082676 A1 | 3/2009 | Bennison |
| 2009/0095679 A1 | 4/2009 | Demers et al. |
| 2009/0292236 A1 | 11/2009 | Kleinekofort |
| 2010/0192686 A1 | 8/2010 | Kamen et al. |
| 2010/0234787 A1 | 9/2010 | Masaoka |
| 2011/0021935 A1 | 1/2011 | Ghodrati |
| 2011/0034814 A1 | 2/2011 | Kopperschmidt |
| 2011/0301472 A1 | 12/2011 | Grober et al. |
| 2012/0259585 A1 | 10/2012 | Haynes et al. |
| 2013/0046190 A1 | 2/2013 | Davies |
| 2014/0024954 A1 | 1/2014 | Frinak et al. |

FOREIGN PATENT DOCUMENTS

| | | |
|---|---|---|
| DE | 19848235 | 3/2000 |
| EP | 0121931 | 10/1984 |
| EP | 0232599 | 8/1987 |
| EP | 0248633 B1 | 12/1987 |
| EP | 0300315 | 1/1989 |
| EP | 0328163 A2 | 8/1989 |
| EP | 0332330 | 9/1989 |
| EP | 0361793 | 4/1990 |
| EP | 0895787 | 2/1999 |
| EP | 1472973 | 11/2004 |
| EP | 1736185 | 12/2006 |
| JP | 63-65875 | 3/1988 |
| JP | 11-104233 | 4/1999 |
| JP | 2000-503249 | 3/2000 |
| JP | 2005040518 | 2/2005 |
| JP | 2006/110118 | 4/2006 |
| JP | 2006/110120 | 4/2006 |
| WO | WO 91/00113 | 1/1991 |
| WO | WO 97/10013 | 3/1997 |
| WO | WO 98/20918 A1 | 5/1998 |
| WO | WO 99/29356 | 6/1999 |
| WO | WO 00/18451 | 4/2000 |
| WO | WO 02/102441 | 12/2002 |
| WO | WO 03/002174 | 1/2003 |
| WO | WO 03/006944 | 1/2003 |
| WO | WO 03/058608 | 7/2003 |
| WO | WO 2005/019416 | 3/2005 |
| WO | WO 2006/122001 | 11/2006 |

OTHER PUBLICATIONS

Widrow et al., "Adaptive Signal Processing," Library of Congress Cataloging in Publication Data, Applications Part IV, Adaptive Interference Canceling, Chapter 12, Cover Pages, pp. 316-323, 1985, ISBN 0-13-004029-0.

\* cited by examiner

METHODS AND DEVICES FOR MONITORING THE INTEGRITY OF A FLUID CONNECTION

PRIORITY CLAIM

This application is a continuation application of U.S. patent application Ser. No. 13/001,314, entitled, "Methods and Devices for Monitoring the Integrity of a Fluid Connection", filed on Dec. 23, 2010, which is a U.S. National Phase of International Application No. PCT/EP2009/004640, filed on Jun. 26, 2009, which claims priority to U.S. Provisional Application No. 61/075,774, filed on Jun. 26, 2008, and Swedish Patent Application No. 0801517-4, filed on Jun. 26, 2008, the entire contents of each of which are incorporated herein by reference.

TECHNICAL FIELD

The present invention generally relates to monitoring of fluid connections, and in particular to monitoring the integrity of a fluid connection based on a pressure measurement. The present invention is e.g. applicable in arrangements for extracorporeal blood treatment.

BACKGROUND

In extracorporeal blood treatment, blood is taken out of a patient, treated and then reintroduced into the patient by means of an extracorporeal blood flow circuit. Generally, the blood is circulated through the circuit by one or more pumping devices. The circuit is connected to a blood vessel access of the patient, typically via one or more access devices, such as needles or catheters, which are inserted into the blood vessel access. Such extracorporeal blood treatments include hemodialysis, hemodiafiltration, hemofiltration, plasmapheresis, etc.

In extracorporeal blood treatment, it is vital to minimize the risk for malfunctions in the extracorporeal blood flow circuit, since these may lead to a potentially life-threatening condition of the patient. Serious conditions may arise if the extracorporeal blood flow circuit is disrupted, e.g. by an access device for blood extraction (e.g. an arterial needle/catheter) coming loose from the blood vessel access, causing air to be sucked into the circuit, or by an access device for blood reintroduction (e.g. a venous needle/catheter) coming loose from the blood vessel access, causing the patient to be drained of blood within minutes. Other malfunctions may be caused by the blood vessel access becoming blocked or obstructed, or by the access device being positioned too close to the walls of the blood vessel access.

To this end, an apparatus for extracorporeal blood treatment may include one or more surveillance devices that monitor the integrity of the blood flow circuit and issue an alarm and/or cause appropriate action to be taken whenever a potentially dangerous situation is detected. Such surveillance devices may operate on measurement signals from one or more pressure sensors in the circuit. Conventionally, the monitoring is carried out by comparing one or more measured average pressure levels with one or more threshold values and/or by monitoring the presence of air bubbles using an air detector in the circuit. For example, failure in the blood extraction may involve air being introduced into the circuit, whereby the measured average pressure may approach atmospheric pressure, or the blood flow being blocked or obstructed, whereby the measured average pressure may drop to a low level. A failure in the reintroduction of blood may be detectable as a decrease in the measured average pressure. However, it may be difficult to set appropriate threshold values, since the average pressure in the circuit may vary between treatments, and also during a treatment, e.g. as a result of the patient moving. Further, if an access device comes loose and gets stuck in bed sheets or the patient's clothes, the measured average pressure might not change enough to indicate the potentially dangerous situation.

To increase the monitoring precision, WO 97/10013 proposes detecting, as one of several options, a heart signal in the measured pressure and using the heart signal as an indicator of the integrity of a fluid connection between an extracorporeal blood flow circuit and a blood vessel access. The heart signal represents a pressure wave which is produced by the patient's heart and transmitted from the patient's circulatory system to the extracorporeal blood flow circuit via the blood vessel access. Malfunctions in the fluid connection will disturb the transmission of the heart-generated pressure wave to the circuit, causing the heart signal to change or even disappear. The measured pressure may also include a strong pressure wave produced by the blood pump in the extracorporeal blood flow circuit. In WO 97/10013, the monitoring involves filtering a measured pressure signal to remove the frequency components that originate from the blood pump, and then detecting the heart signal by analysing the filtered pressure signal. The amplitude of the filtered pressure signal is then taken as an indication of the integrity of the fluid connection.

US2005/0010118 proposes a solution which involves applying a frequency analysis to a measured pressure signal to generate a frequency spectrum, removing a frequency component that originates from the blood pump, and identifying a frequency component caused by the patient's heart. Anomalies of the blood vessel access are monitored based on the intensity level of the frequency component caused by the patient's heart.

Corresponding needs to monitor the integrity of a fluid connection between first and second fluid containing systems may arise in other fields of technology.

SUMMARY

It is an object of the invention to at least partly overcome one or more of the above-identified limitations of the prior art. Specifically, it is an object to provide an alternative or complementary technique for monitoring the integrity of a fluid connection between first and second fluid containing systems using a pressure measurement, preferably with an improved robustness and/or an increased certainty of detecting a malfunction in the fluid connection.

This and other objects, which will appear from the description below, are at least partly achieved by means of methods, devices, and a computer program product according to the independent claims, embodiments thereof being defined by the dependent claims.

A first aspect of a first inventive concept of the invention is a method for monitoring the integrity of a fluid connection between first and second fluid containing systems based on at least one time-dependent measurement signal from at least one pressure sensor in the first fluid containing system, wherein the first fluid containing system comprises a first pulse generator, and the second fluid containing system comprises a second pulse generator, and wherein said at least one pressure sensor is arranged to detect first pulses originating from the first pulse generator and second pulses originating from the second pulse generator, said method comprising: receiving said at least one measurement signal; generating, based on said at least one measurement signal, a time-dependent monitoring signal in which the first pulses are essentially eliminated; calculating a parameter value based on signal values within a time window in the monitoring signal, the parameter value representing a distribution of the signal values; and determining the integrity of the fluid connection based at least partly on the parameter value.

In one embodiment, said calculating comprises: calculating the parameter value as a statistical dispersion measure of the signal values within the time window. The statistical dispersion measure may include at least one of: a standard deviation, a variance, a coefficient of variation, a sum of differences, an energy, a power, a sum of absolute deviations from an average value, and an average of absolute differences from an average value.

In one embodiment, said calculating comprises: matching the signal values within the time window to a predicted temporal signal profile of a second pulse. The parameter value may be a correlation value resulting from said matching.

In one embodiment, said calculating comprises: calculating a cross-correlation between the signal values within the time window and the predicted temporal signal profile; and identifying a maximum correlation value in the cross-correlation; wherein said determining comprises: comparing the maximum correlation value to a threshold value.

In one embodiment, said calculating comprises: obtaining a time point of the maximum correlation value, and validating the maximum correlation value by comparing the time point to a predicted time point.

In one embodiment, the method further comprises the step of obtaining a reference pressure signal from a reference sensor in the first fluid containing system, wherein the reference sensor is arranged to detect said second pulses even if the fluid connection is compromised, and calculating the predicted temporal signal profile based on the reference pressure signal. Additionally, the method may further comprise the steps of calculating a magnitude value indicative of the magnitude of the second pulses in the reference pressure signal, and comparing the magnitude value to a limit, wherein the step of calculating the predicted temporal signal profile based on the reference pressure signal may be conditioned upon said step of comparing. Alternatively or additionally, the step of calculating the predicted temporal signal profile may comprise adjusting for a difference in transit time between the reference sensor and said at least one pressure sensor, wherein the difference in transit time may be given by a predefined value, or may be calculated based on a difference in fluid pressure between the location of the reference sensor and said at least one pressure sensor.

In one embodiment, the time window is selected so as to contain at least one second pulse. The length of the time window may be chosen to exceed a maximum pulse repetition interval of the second pulse generator.

In one embodiment, the time window is chosen based on timing information indicative of the timing of the second pulses in said at least one measurement signal.

In one embodiment, said monitoring signal is generated by: filtering said at least one measurement signal to remove the first pulses; deriving, based on timing information indicative of the timing of the second pulses in said at least one measurement signal, a set of signal segments in the thus-filtered measurement signal(s); and aligning and adding the signal segments, based on the timing information, to generate said monitoring signal.

In one embodiment, said calculating comprises: identifying a candidate second pulse in the monitoring signal and a corresponding candidate time point; and validating the candidate second pulse based on the candidate time point in relation to timing information indicative of the timing of the second pulses in said at least one measurement signal.

In one embodiment, the timing information is obtained from a pulse sensor coupled to the second fluid containing system.

In one embodiment, the timing information is obtained as a function of the relative timing of second pulses identified based on preceding parameter values.

In one embodiment, the first fluid containing system is an extracorporeal blood flow circuit comprising an arterial access device, a blood processing device, and a venous access device, wherein the second fluid containing system is a human blood system comprising a blood vessel access, wherein the arterial access device is connected to the human blood system, wherein the venous access device is connected to the blood vessel access to form the fluid connection, wherein the first pulse generator is a pumping device arranged in the extracorporeal blood flow circuit to pump blood from the arterial access device through the blood processing device to the venous access device, wherein said at least one measurement signal comprises at least one venous measurement signal derived from at least one venous pressure sensor located downstream of the pumping device, and at least one arterial measurement signal derived from at least one arterial pressure sensor located upstream of the pumping device, and wherein the monitoring signal is generated based on said at least one venous measurement signal, said method comprising: identifying at least one second pulse in said at least one arterial measurement signal; and calculating the timing information from the thus-identified second pulse(s).

In one embodiment, the method further comprises: intermittently turning off the first pulse generator; identifying at least one second pulse in said at least one measurement signal; and calculating the timing information from the thus-identified second pulse.

In one embodiment, the method further comprises: identifying a set of candidate second pulses based on said at least one measurement signal; deriving a sequence of candidate time points based on the set of candidate second pulses; validating the sequence of candidate time points against a temporal criterion; and calculating the timing information as a function of the thus-validated sequence of candidate time points.

In one embodiment, the first fluid containing system is an extracorporeal blood processing system comprising an access device, wherein the second fluid containing system is a human blood system comprising a blood vessel access, and wherein a connection between the access device and the blood vessel access forms the fluid connection.

A second aspect of the first inventive concept of the invention is a computer program product comprising instructions for causing a computer to perform the method according to the first aspect.

A third aspect monitoring the integrity of a fluid connection between first and second fluid containing systems based on at least one time-dependent measurement signal from at least one pressure sensor in the first fluid containing system, wherein the first fluid containing system comprises a first pulse generator, and the second fluid containing system comprises a second pulse generator, and wherein said at least one pressure sensor is arranged to detect first pulses originating from the first pulse generator and second pulses originating from the second pulse generator, said device comprising: an input for said at least one measurement signal; and a signal processor connected to said input and comprising a processing module configured to generate, based on said at least one measurement signal, a time-dependent monitoring signal in which the first pulses are essentially eliminated, and to calculate a parameter value based on signal values within a time window in the monitoring signal, the parameter value representing a distribution of the signal values, said signal processor being configured to determine the integrity of the fluid connection based at least partly on the parameter value.

A fourth aspect of the first inventive concept of the invention is a device for monitoring the integrity of a fluid connection between first and second fluid containing systems based on at least one time-dependent measurement signal from at least one pressure sensor in the first fluid containing system, wherein the first fluid-containing system comprises a first pulse generator, and the second fluid containing system comprises a second pulse generator, and wherein said at least one pressure sensor is arranged to detect first pulses originating from the first pulse generator and second pulses originating from the second pulse generator, said device comprising: means for receiving said at least one measurement signal; means for generating, based on said at least one measurement signal, time-dependent monitoring signal in which the first pulses are essentially eliminated; means for calculating a parameter value based on signal values within a time window in the monitoring signal, the parameter value representing a distribution of the signal values; and means for determining the integrity of the fluid connection based at least partly on the parameter value.

Embodiments of the third and fourth aspects of the first inventive concept may correspond to the above-identified embodiments of the first aspect of the first inventive concept.

A first aspect of a second inventive concept of the invention is a method for monitoring the integrity of a fluid connection between first and second fluid containing systems based on at least one time-dependent measurement signal from at least one pressure sensor in the first fluid containing system, wherein the first fluid containing system comprises a first pulse generator, and the second fluid containing system comprises a second pulse generator, and wherein said at least one pressure sensor is arranged to detect first pulses originating from the first pulse generator and second pulses originating from the second pulse generator, said method comprising: receiving said at least one measurement signal; obtaining timing information indicative of the timing of the second pulses in said at least one measurement signal; processing said at least one measurement signal based on the timing information, to calculate a parameter value indicative of presence or absence of the second pulses; and determining the integrity of the fluid connection based at least partly on the parameter value.

In one embodiment, said processing comprises: locating a time window in the measurement signal, or a monitoring signal obtained therefrom, based on the timing information; and calculating the parameter value based on the signal values within said time window.

In one embodiment, said processing further comprises: selecting the length of the time window based on the timing information.

In one embodiment, said processing comprises: generating a time-dependent monitoring signal by filtering said at least one measurement signal to remove the first pulses; wherein the parameter value is calculated based on the monitoring signal.

In one embodiment, said generating further comprises: selecting a set of signal segments in the thus-filtered measurement signal(s); and aligning and adding the signal segments, based on the timing information, to generate the monitoring signal.

In one embodiment, said calculating comprises: identifying a candidate second pulse in the monitoring signal and a corresponding candidate time point; and validating the candidate second pulse based on the candidate time point in relation to the timing information.

In one embodiment, the timing information is obtained from a pulse sensor coupled to the second fluid containing system.

In one embodiment, the timing information is obtained as a function of the relative timing of second pulses identified based on preceding parameter values.

In one embodiment, the method further comprises the step of obtaining a reference pressure signal from a reference sensor in the first fluid containing system, wherein the reference sensor is arranged to detect said second pulses even if the fluid connection is compromised, and wherein said step of obtaining the timing information comprises: identifying at least one second pulse in the reference pressure signal and obtaining an estimated difference in arrival time between the reference sensor and said at least one pressure sensor. The estimated difference in arrival time may be given by a predefined value, or may be calculated based on a difference in fluid pressure between the location of the reference sensor and said at least one pressure sensor. Additionally, the method may further comprise the steps of calculating a magnitude value indicative of the magnitude of said at least one second pulse in the reference pressure signal, and comparing the magnitude value to a limit, wherein the step of obtaining an estimated difference in arrival time may be conditioned upon said step of comparing.

In one embodiment, the first fluid containing system is an extracorporeal blood flow circuit comprising an arterial access device, a blood processing device, and a venous access device, wherein the second fluid containing system is a human blood system comprising a blood vessel access, wherein the arterial access device is connected to the human blood system, wherein the venous access device is connected to the blood vessel access to form the fluid connection, wherein the first pulse generator is a pumping device arranged in the extracorporeal blood flow circuit to pump blood from the arterial access device through the blood processing device to the venous access device, wherein said at least one measurement signal comprises at least one venous measurement signal derived from at least one venous pressure sensor located downstream of the pumping device, and at least one arterial measurement signal derived from at least one arterial pressure sensor located upstream of the pumping device, and wherein the monitoring signal is generated based on said at least one venous measurement signal, said method comprising: identifying at least one second pulse in said at least one arterial measurement signal; and calculating the timing information from the thus-identified second pulse(s).

In one embodiment, the method further comprises: intermittently turning off the first pulse generator; identifying at least one second pulse in said at least one measurement signal; and calculating the timing information from the thus-identified second pulse.

In one embodiment, the method further comprises: identifying a set of candidate second pulses based on said at least one measurement signal; deriving a sequence of candidate time points based on the set of candidate second pulses; validating the sequence of candidate time points against a temporal criterion; and calculating the timing information as a function of the thus-validated sequence of candidate time points.

In one embodiment, said obtaining further comprises: identifying a set of candidate second pulses based on said at least one measurement signal; deriving a sequence of candidate time points based on the set of candidate second pulses; generating a set of validated candidate second pulses by validating the sequence of candidate time points against a temporal criterion; wherein said processing comprises: calculating a set of average representations, each average representation being formed by aligning and adding signal segments of said at least one measurement signal that correspond to a unique combination of validated candidate second pulses; and calculating the parameter value for each of said average representations; and wherein said determining comprises comparing a maximum parameter value to a threshold value.

In one embodiment, the parameter value represents a distribution of signal values.

A second aspect of the second inventive concept of the invention is a computer program product comprising instructions for causing a computer to perform the method according to the first aspect of the second inventive concept.

A third aspect of the second inventive concept of the invention is a device for monitoring the integrity of a fluid connection between first and second fluid containing systems based on at least one time-dependent measurement signal from at least one pressure sensor in the first fluid containing system, wherein the first fluid containing system comprises a first pulse generator, and the second fluid containing system comprises a second pulse generator, and wherein said at least one pressure sensor is arranged to detect first pulses originating from the first pulse generator, and second pulses originating from the second pulse generator, said device comprising: an input for said at least one measurement signal; and a signal processor connected to said input and comprising a processing module configured to obtain timing information indicative of the timing of the second pulses in said at least one measurement signal, and to process said at least one measurement signal based on the timing information so as to generate a parameter value indicative of presence or absence of the second pulses, said signal processor being configured to determine the integrity of the fluid connection based at least partly on the parameter value.

A fourth aspect of the second inventive concept of the invention is a device for monitoring the integrity of a fluid connection between first and second fluid containing systems based on at least one time-dependent measurement signal from at least one pressure sensor in the first fluid containing system, wherein the first fluid containing system comprises a first pulse generator, and the second fluid containing system comprises a second pulse generator, and wherein said at least one pressure sensor is arranged to detect first pulses originating from the first pulse generator, and second pulses originating from the second pulse generator, said device comprising: means for receiving said at least one measurement signal; means for obtaining timing information indicative of the timing of the second pulses in said at least one measurement signal; means for processing said at least one measurement signal based on the timing information, to generate a parameter value indicative of presence or absence of the second pulses, and means for determining the integrity of the fluid connection based at least partly on the parameter value.

Embodiments of the third and fourth aspects of the second inventive concept may correspond to the above-identified embodiments of the first aspect of the second inventive concept.

Still other objectives, features, aspects and advantages of the present invention will appear from the following detailed description, from the attached claims as well as from the drawings.

BRIEF DESCRIPTION OF THE FIGURES

Embodiments of the inventive concepts will now be described in more detail with reference to the accompanying schematic drawings.

DETAILED DESCRIPTION

In the following, inventive concepts and associated elements will be described with reference to fluid containing systems in general. Thereafter, the inventive concepts will be further exemplified in the context of systems for extracorporeal blood treatment.

Throughout the following description, like elements are designated by the same reference signs.

GENERAL

Figure 1:
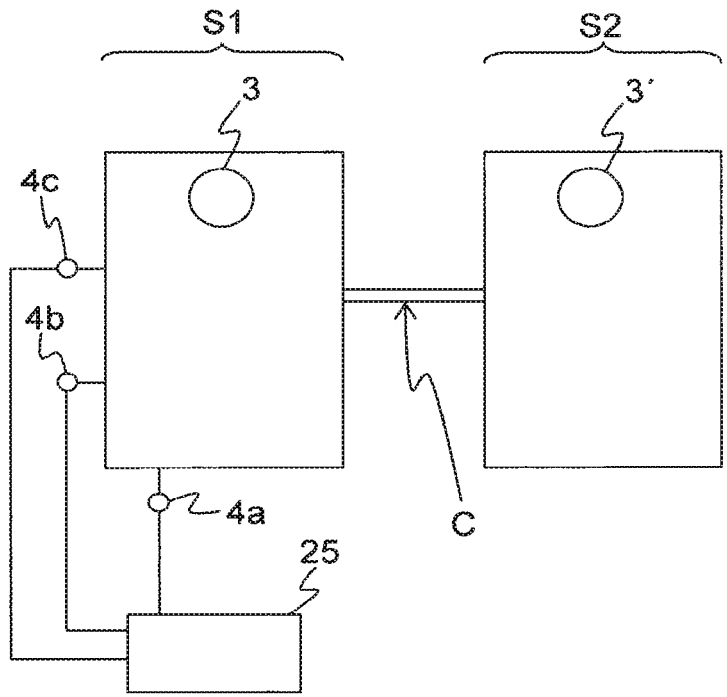
FIG. 1 is a schematic view of a general fluid arrangement in which the inventive concepts may be used for monitoring the integrity of a fluid connection.

FIG. 1 illustrates a general fluid arrangement in which a fluid connection C is established between a first fluid containing system 51 and a second fluid containing system S2. The fluid connection C may or may not transfer fluid from one system to the other. A first pulse generator 3 is arranged to generate a series of pressure waves in the fluid within the first system 51, and a second pulse generator 3' is arranged to generate a series of pressure waves in the fluid within the second system S2. A pressure sensor 4c is arranged to measure the fluid pressure in the first system 51. As long as the fluid connection C is intact, pressure waves generated by the second pulse generator 3' will travel from the second system S2 to the first system 51, and thus second pulses originating from the second pulse generator 3' will be detected by the pressure sensor 4c in addition to first pulses originating from the first pulse generator 3. It is to be noted that either one of the first and second pulse generators 3, 3' may include more than one pulse-generating device. Further, any such pulse-generating device may or may not be part of the respective fluid containing system 51, S2.

The fluid arrangement of FIG. 1 further includes a surveillance device 25 which is connected to the pressure sensor 4c, and possibly to one or more further pressure sensors 4a, 4b, as indicated in FIG. 1. Thereby, the surveillance device 25 acquires one or more measurement signals that are time-dependent to provide a real time representation of the fluid pressure in the first system 51. The surveillance device 25 monitors the integrity of the fluid connection C, based on the principle that the presence of second pulses indicates that the fluid connection C is intact, whereas absence of second pulses indicates that the fluid connection C is compromised. The absence of second pulses may bring the surveillance device 25 to issue an alarm or warning signal, and/or alert a control system of the first or second fluid containing systems S1, S2 to take appropriate action.

The surveillance device 25 is thus configured to continuously process the time-dependent measurement signal(s) to determine whether second pulses are present or not. Typically, the determination involves analyzing the measurement signal(s), or a preprocessed version thereof, in the time domain to calculate a value of an evaluation parameter which is indicative of the presence or absence of second pulses in the measurement signal(s). Depending on implementation, the surveillance device 25 may use digital components or analog components, or a combination thereof, for receiving and processing the measurement signal(s).

In the context of the present disclosure, "absence" of a pulse may imply that the pulse has disappeared, or at least that it has decreased sufficiently in magnitude compared to the pulse deemed to be "present". The assessment of presence or absence may involve calculating an evaluation parameter value based on the measurement signal(s) and comparing the parameter value to a threshold value.

First Inventive Concept

Figure 2:
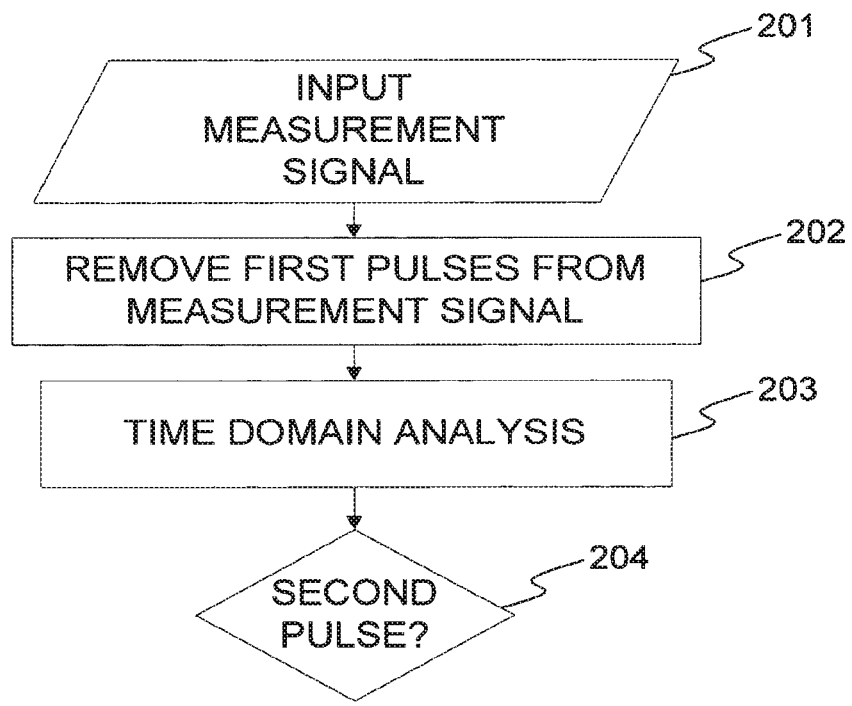
FIG. 2 is a flow chart of a monitoring process according to a first inventive concept.

FIG. 2 is a flow chart that illustrates steps of a monitoring process according to a first inventive concept. A measurement signal is received (step 201) and subjected to a filtering process (step 202) that essentially removes the first pulses from the measurement signal, while leaving at least part of the second pulses intact. The filtered measurement signal is then subjected to a time domain analysis (step 203), in which a value of an evaluation parameter is calculated based on signal values within a time window in the filtered measurement signal, which is denoted "evaluation segment" in the following. The calculation is typically designed such that the evaluation parameter represents the distribution of signal values within the evaluation segment. Based on the resulting value of the evaluation parameter, it is decided (step 204) whether the fluid connection is intact or not, typically by comparing the resulting value to a threshold value.

For continuous surveillance, a time sequence of evaluation parameter values is calculated based on a time sequence of evaluation segments obtained from the measurement signal. These evaluation segments may be overlapping or non-overlapping in time. In one embodiment, individual sections of the measurement signal are acquired, filtered and analyzed, one after the other. Each evaluation segment may correspond to one such section of the measurement signal; the time window is thus applied already when the measurement signal is acquired. In another embodiment, the measurement signal is continuously acquired and filtered, whereupon evaluation segments are extracted from the filtered signal and analyzed.

Figure 3:
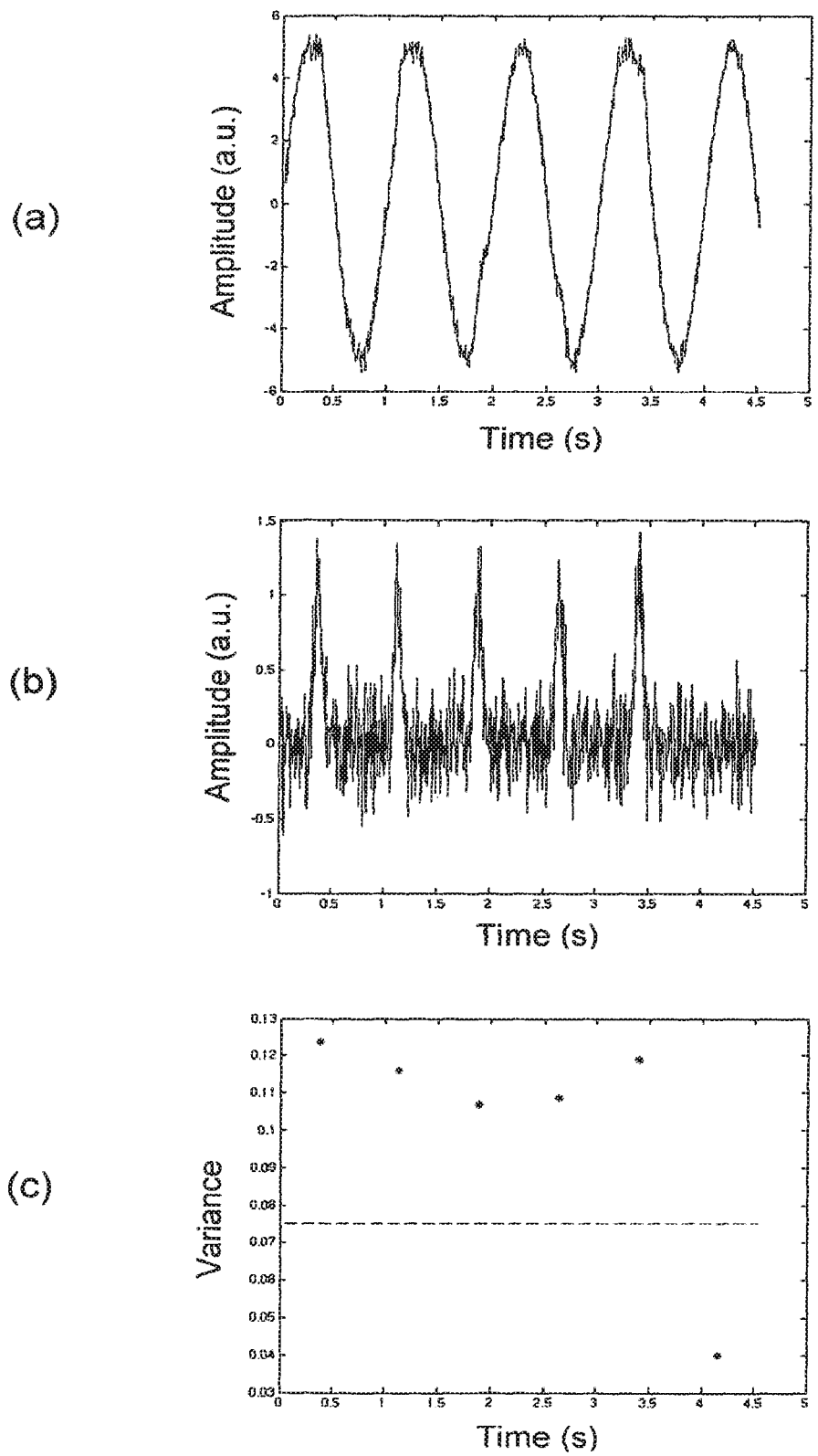
FIG. 3(a) is a plot of the measurement signal as a function of time.
FIG. 3(b) is a plot of the measurement signal in FIG. 3(a) after filtering.
FIG. 3(c) illustrates a statistical dispersion measure calculated for a sequence of time windows in the signal in FIG. 3(b).

FIG. 3(a) shows an example of a time-dependent measurement signal containing first and second pulses with a relative magnitude of 10:1. The first and second pulses have a frequency of 1 Hz and 1.33 Hz, respectively. FIG. 3(b) shows the time-dependent measurement signal after removal of the first pulses, leaving only second pulses and noise. It should be noted that there is an absence of second pulses after about 4 seconds. FIG. 3(c) illustrates a variance measure calculated for a sequence of non-overlapping time windows in the filtered measurement signal in FIG. 3(b), each time window being about 0.75 seconds. Clearly, by using the variance measure as an evaluation parameter, it is possible to detect the absence of the second pulse at the time point of about 4 seconds. An exemplifying threshold value is indicated by a dotted line.

The first inventive concept has the potential of providing a comparatively robust measure of the integrity of the fluid connection C. By analyzing the temporal distribution of signal values within the evaluation segment, an improved tolerance to noise and disturbing signals may be obtained.

Furthermore, compared to techniques that rely on frequency domain analysis of the measurement signal for detecting the presence of second pulses, the first inventive concept may provide an improved tolerance to variations in the pulse repetition interval of the second pulse generator 3', since the first inventive concept relies on a time domain analysis. Such variations may occur, e.g., when the second pulse generator 3' is a human heart, and the second system S2 thus is the blood system of a human. Variations in heart rhythm (heart rate variability, HRV) will cause the peak from the heart in the frequency domain to be smeared out, making it harder to detect. In healthy subjects under calm conditions, HRV may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

As long as the time window is selected such that each evaluation segment contains at least one second pulse, the presence/absence of second pulses will affect the evaluation parameter, if properly chosen. A fixed-length time window may be used, with the length of the time window being chosen with respect to a maximum pulse repetition rate of the second pulse generator 3'. The length of the time window may be set by constraints in the second pulse generator 3' or by a selected performance limit of the surveillance method. Alternatively, the length of the time window and/or the location of the time window in the filtered measurement signal may be selected based on a predicted timing of the second pulse(s) to be detected. The acquisition and use of such a predicted timing ("timing information") will be further exemplified below with reference to the second inventive concept.

Still further, the time domain analysis according to the first inventive concept may allow for faster detection than a frequency domain analysis, since the former may have the ability to detect a single second pulse in the evaluation segment whereas the generation of a frequency spectrum requires a greater number of second pulses in the evaluation segment. Thus, frequency domain analysis may be associated with a greater time lag than time domain analysis.

The evaluation parameter may be calculated as a statistical dispersion measure of the signal values within the evaluation segment. Non-limiting examples of potentially useful statistical dispersion measures include standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|, \text{ or}$$

$$\sum_{i=1}^{n} \sum_{j=1}^{n} |x_i - x_j|,$$

or an energy measure, such as $$\sum_{i=1}^{n} x_i^2,$$

with n being the number of signal values x in the evaluation segment. Yet other examples include a measure based on a sum of absolute differences from an average value m, with the average value m being calculated for the signal values in the evaluation segment using any suitable function, such as arithmetic mean, geometric mean, median, etc. It is to be noted that all of the above suggested dispersion measures also include normalized and/or weighted variants thereof.

As an alternative or supplement to calculating a statistical dispersion measure, the evaluation parameter may result from a matching procedure, in which the evaluation segment is matched to one or more predicted signal profiles of a second pulse. Preferably, but not necessarily, each predicted signal profile represents a single second pulse. Typically, the matching procedure involves convolving or cross-correlating the evaluation segment and the predicted signal profile, and the evaluation parameter value is a resulting correlation value, typically the maximum correlation value.

Figure 4:
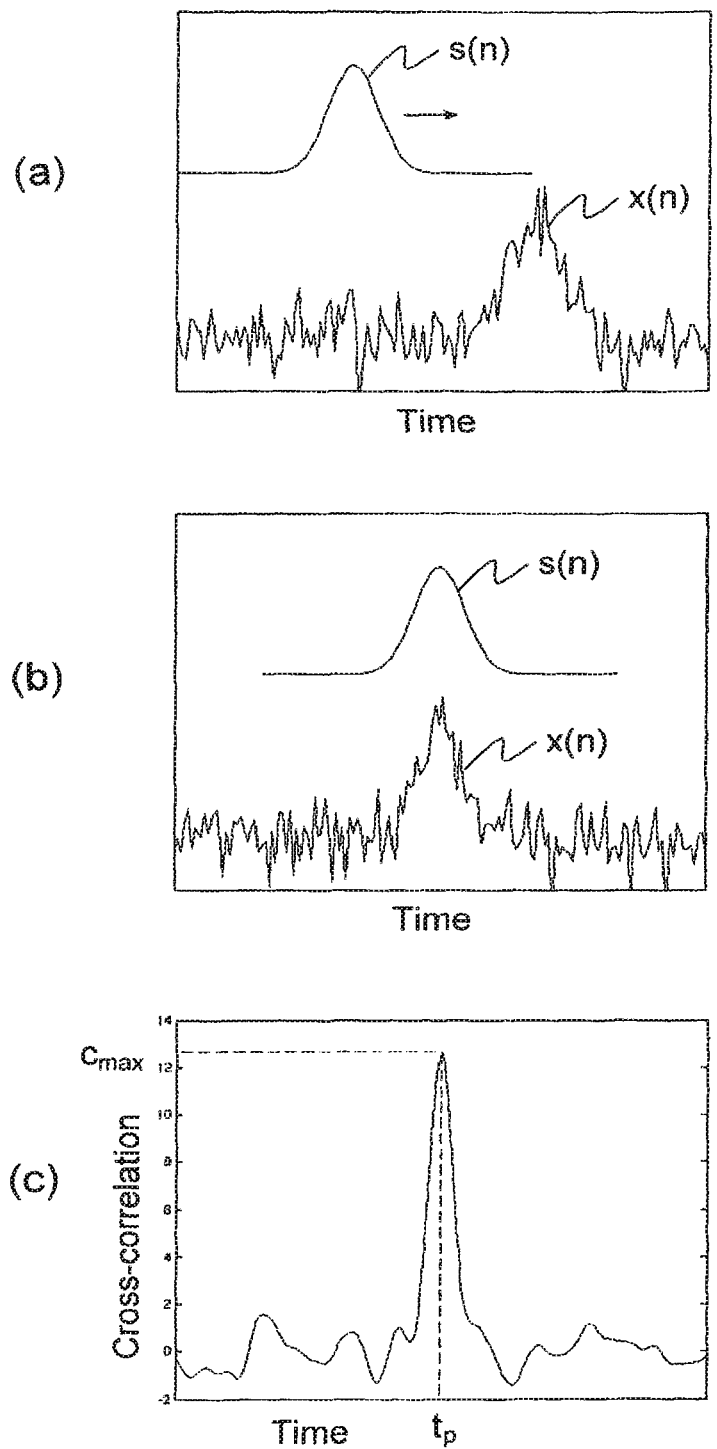
FIG. 4(a) illustrates a matching procedure between a measurement signal and a predicted signal profile.
FIG. 4(b) illustrates the position of best match.
FIG. 4(c) is a correlation curve resulting from the matching procedure in FIG. 4(a).

A matching procedure based on cross-correlation is further exemplified in FIGS. 4(a)-4(c). The matching procedure is used to distinguish between the hypotheses $H_0$: x(n)=w(n)
$H_1$: x(n)=s(n)+w(n)

with x(n) being the evaluation segment, w(n) being an error signal representing disturbances introduced by noise/signal interference/measurement errors, etc., and s(n) being the predicted signal profile of the second pulse. If $H_1$ is deemed more likely than $H_0$, then a second pulse has been identified and the fluid connection C is deemed intact. If $H_0$ is deemed more likely than $H_1$, then a second pulse cannot be identified and the fluid connection C may be compromised.

FIG. 4(a) is a graph showing an example of a predicted signal profile s(n) and an evaluation segment x(n). In this particular example, the evaluation segment has a signal-to-noise ratio (SNR) of 4.8 dB, i.e. the energy of the signal profile s(n) is 3 times the energy of the error signal w(n). During the cross-correlation, the signal profile s(n) is slid in a number of time steps along the time axis, as indicated by arrow in FIG. 4(a), and the integral of the product s(n)–x(n) is calculated for each time step. The cross-correlation thus results in a time sequence of correlation values, with the maximum correlation value indicating the time point of best match between x(n) and s(n). FIG. 4(b) illustrates the relative position between x(n) and s(n) at the time point for best match, and FIG. 4(c) illustrates the resulting correlation values as a function of said time steps. The magnitude of the maximum correlation value, optionally calculated as a weighted average within a range around the maximum correlation value ($c_{max}$), may thus be used to distinguish between the above hypotheses.

As indicated in FIG. 4(c), the matching procedure not only identifies the presence of a second pulse, it also provides an indication of the location of the second pulse in the evaluation segment, given by the time point ($t_p$) for the maximum correlation value ($c_{max}$). This time point may be used to assess the reliability of the determined maximum correlation value, by comparing this time point to a predicted time point. Such a predicted time point may be obtained from aforesaid timing information, as will be further explained below in relation to the second inventive concept.

The predicted signal profile may be generated as an average of a number of recordings of second pulses. For example, it may be generated by averaging a number of evaluation segments, before and/or during the monitoring process.

To improve the signal quality of the predicted profile, with or without averaging, the measurement signal may be acquired while the first pulse generator is stopped, whereby the measurement signal is free of first pulses. Thus, the first pulse generator may be intermittently stopped during the monitoring process for calculation of an updated signal profile of the second pulses.

In another variant, the predicted signal profile is obtained from one or more reference signals originating from a reference pressure sensor (e.g. any one of pressure sensors 4a-4c in FIG. 1) in the first system. Such a reference pressure sensor is suitably arranged to detect second pulses even if the fluid connection is compromised, e.g. via a second fluid connection between the first and second fluid containing systems. The reference pressure sensor may be installed to be isolated from the first pulses, such that the reference signal is essentially free of first pulses. Alternatively, if the reference signal includes both first and second pulses, the reference signal may be subjected to a filtering process (e.g. according to step 202 in FIG. 2) to remove the first pulses while leaving the second pulses intact in the reference signal. An example of such a reference pressure sensor is an arterial pressure sensor in an extracorporeal blood flow circuit, to be further described below. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient.

In one specific implementation, the reference signal is obtained continuously or intermittently during the monitoring process, and the predicted signal profile is continuously or intermittently calculated based on the reference signal. Thus, in the context of the above-mentioned extracorporeal blood flow circuit, the integrity of the venous-side fluid connection may be monitored by continuously matching evaluation segments from the venous pressure sensor against a predicted signal profile obtained from the arterial pressure sensor. It is even conceivable that the predicted signal profile is updated for each evaluation segment (denoted "synchronous monitoring" in the following). The matching procedure may benefit from the use of timing information, as will be further explained below in relation to the second inventive concept. Alternatively, the predicted signal profile may be pre-generated, e.g. by averaging recordings of second pulses from a number of fluid arrangements, similar to the one that is being monitored (cf. FIG. 1). Optionally, such a pre-generated signal profile may be adapted to specifics of the fluid arrangement to be monitored, by applying a mathematical model taking into account arrangement-specific parameters, such a type of fluid connection, flow rate, fluid characteristics, etc. Alternatively, the predicted signal profile may be obtained entirely by mathematical modelling based on arrangement-specific parameters. According to yet another alternative, a standard profile is used as predicted signal profile, e.g. a bell-shaped function such as a Gaussian distribution function.

In order to improve the detection of second pulses, it is conceivable to subject the filtered measurement signal/evaluation segment to a signal enhancement process, which removes high-frequency components (cf. error signal $w(n)$), before calculation of the evaluation parameter value. Such a signal enhancement process may involve subjecting the filtered measurement signal/evaluation segment to a low-pass filtering. However, a more significant improvement in SNR of the evaluation segment may be achieved by averaging several consecutive second pulses in the filtered measurement signal, again based on the above-mentioned predicted timing of the second pulse(s) (i.e. timing information). Such a signal enhancement process would thus involve using the predicted timing to identify a set of second pulse segments in the filtered measurement signal, aligning the second pulse segments in the time domain based on the predicted timing, and generating an average representation by summing the aligned signal values for each time value in the time domain. Optionally, the average representation is normalized by the number of second pulse segments to generate a true average. The average representation may then be used as the above-mentioned evaluation segment, or the evaluation segment may be extracted from a time window within the average representation.

Figure 5:
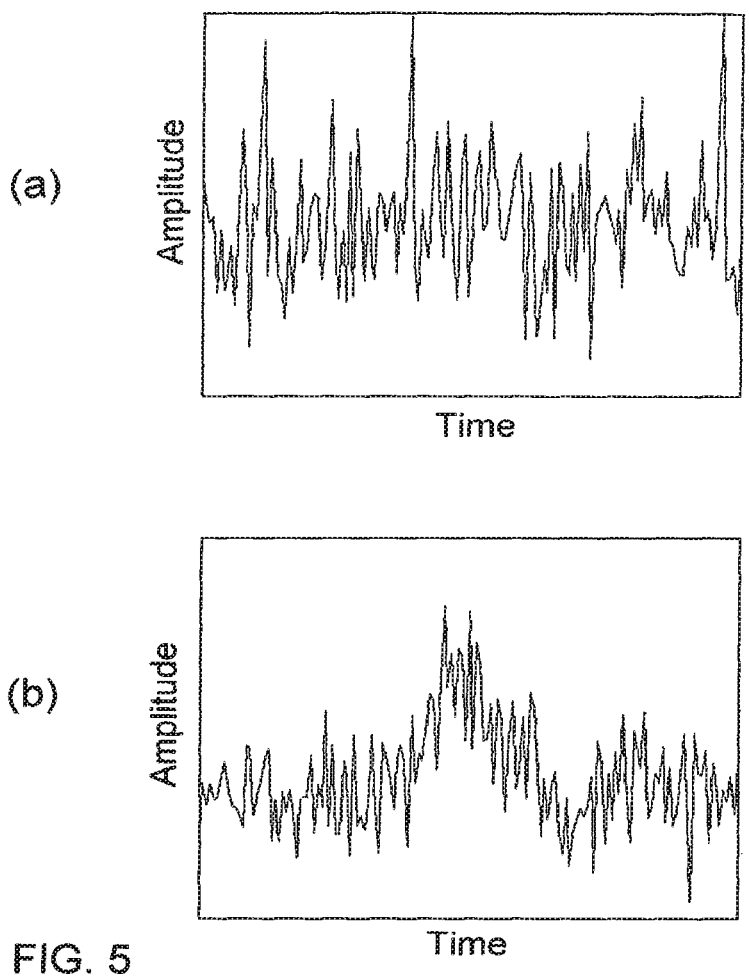
FIG. 5(a) is a plot of a signal segment containing a second pulse.
FIG. 5(b) is plot of an evaluation segment generated by averaging ten signal segments.

The signal enhancement process is further exemplified in FIGS. 5(*a*)-5(*b*). FIG. 5(*a*) is a time domain representation of a filtered measurement signal $x(n)=s(n)+w(n)$ with a SNR of $-9$ dB, i.e. the energy of the error signal $w(n)$ is 8 times the energy of the signal profile $s(n)$, making time domain analysis for detection of the second pulse difficult, if not impossible. FIG. 5(*b*) is a time domain representation after averaging of 10 different second pulse segments similar to the one in FIG. 5(*a*). Clearly, the SNR has been improved significantly, allowing a second pulse to be detected using time domain analysis.

It is to be understood that the monitoring process of FIG. 2 may operate on more than one measurement signal, if the fluid arrangement to be monitored includes more than one pressure sensor (cf. 4*a*, 4*b* in FIG. 1). In such a configuration, the above-described signal enhancement process may involve using aforesaid timing information to identify and average second pulse segments from at least two filtered measurement signals originating from different pressure sensors. Thus, the second pulse segments may be extracted from plural time windows in each measurement signal, and/or from one or more time windows in different measurement signals.

The filtering process according to step 202 in FIG. 2 aims at removing the first pulses from the measurement signal to such an extent that the second pulses can be detected by the subsequent time domain analysis (step 203). For example, a comb filter and/or a combination of band-stop or notch filters, typically cascade coupled, may be operated on the measurement signal to block out all frequency components originating from the first pulse generator 3. Alternatively, such blocking may be achieved by the use of one or more adaptive filters and notch-equivalent filters, e.g. as disclosed in aforesaid WO 97/10013. In yet another alternative embodiment, the measurement signal is processed in the time domain to cancel the first pulses. In such an embodiment, a standard signal profile of the 25 first pulses may be obtained, which is then subtracted from the measurement signal at suitable amplitude and phase. The phase is indicated by phase information which may be obtained from a signal generated by a phase sensor coupled to the first pulse generator 3, or from a control signal for the first pulse generator 3. The standard signal profile may be obtained from one or more of the pressure sensors 4*a*-4*c* in the first fluid containing circuit S1, suitably by identifying and averaging a set of first pulse segments in the measurement signal(s) similarly to the above-mentioned signal enhancement process. The standard signal profile may or may not be updated intermittently during the monitoring process. Alternatively, a predetermined standard signal profile is used, which optionally may be modified according to a mathematical model accounting for wear in the first pulse generator, fluid flow rates, tubing dimensions, speed of sound in the fluid, etc. It should be noted that by filtering the measurement signal in the time domain, instead of the frequency domain, it is possible to eliminate the first pulses and still retain the second pulses, even if the first and second pulses overlap in the frequency domain.

Second Inventive Concept

Figure 6:
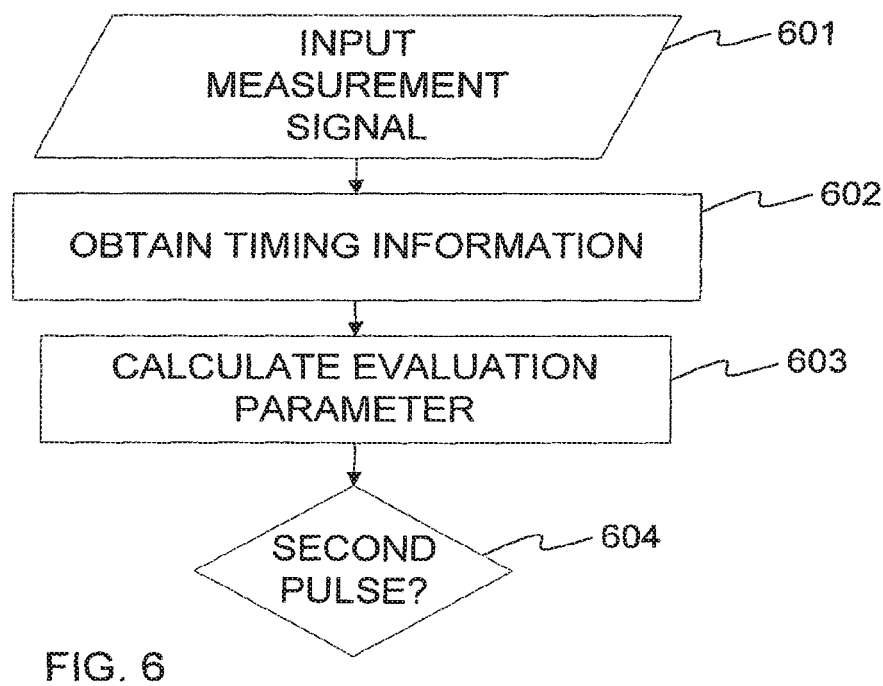
FIG. 6 is a flow chart of a monitoring process according to a second inventive concept.

FIG. 6 is a flow chart that illustrates steps of a monitoring process according to a second inventive concept. In this process, a measurement signal is received (step 601) and timing information is obtained, from the measurement signal or otherwise (step 602). The timing information is indicative of the timing of second pulses in the measurement signal.

Subsequently, the measurement signal is processed (step 603) based on the timing information, to calculate a value of an evaluation parameter which is indicative of the presence or absence of a second pulse in the measurement signal. Based on the resulting value of the evaluation parameter, it is decided (step 604) whether the fluid connection is intact or not, typically by comparing the resulting value to a threshold value.

Thus, in the second inventive concept, timing information indicates the expected position of a second pulse in the measurement signal. This additional information may allow the second pulse to be identified from other types of signal features, e.g. different/simpler evaluation parameters, and/or it may allow for an increased reliability in detecting presence/absence of second pulses.

Furthermore, as explained above, the provision of timing information allows for signal enhancement by identifying and averaging second pulse segments in one or more measurement signals. The signal enhancement may increase the SNR of the measurement signal, allowing for the use of a rudimentary measure as evaluation parameter, such as signal amplitude, local maximum, local average, etc. This may serve to improve the processing speed and/or allow for less sophisticated detection equipment.

It is to be understood that the second inventive concept can be combined with any of the features of the first inventive concept. For example, the measurement signal may be filtered to remove first pulses, and the evaluation parameter may be calculated for an evaluation segment given by signal values within a time window in the filtered measurement signal. Also, any one of the evaluation parameters suggested in relation to the first inventive concept is equally applicable to the second inventive concept. It is to be noted, however, that the filtering of the measurement signal is not an essential feature of the second inventive concept, since the use of timing information may allow second pulses to be detected in the measurement signal even in the presence of first pulses.

The second inventive concept may also improve the detection speed, since the timing information may provide a predicted time point for the second pulse in the measurement signal/filtered measurement signal/evaluation segment. Thereby, the number of signal values that need to be processed for calculation of the evaluation parameter value may be reduced. For example, the aforesaid matching procedure may be simplified, since the correlation between the predicted signal profile and the evaluation segment need only be calculated for the predicted time point, or a confined time range around this predicted time point. Correspondingly, the calculation of a statistical dispersion measure or the abovementioned rudimentary measure may be simplified, since the provision of timing information makes it possible to reduce the size of the time window for extracting the evaluation segment, while still ensuring that each evaluation segment includes at least one second pulse. For example, the size of the time window may be reduced if the timing information indicates a shortened pulse interval between the second pulses, and/or the time window may be centered on the predicted time point of each second pulse.

Still further, the second inventive concept allows for assessing the reliability of a calculated evaluation parameter value, by comparing a time point associated with the evaluation parameter value with a predicted time point given by the timing information. For example, the time point for a maximum correlation value obtained in the aforesaid matching procedure may be compared with a predicted time point for a second pulse. If these time points deviate too much, the monitoring process may determine that a second pulse is absent, even though the magnitude of the correlation value might indicate presence of a second pulse.

The timing information may be obtained in any one of a plurality of different ways. For example, the timing information may be extracted from the output signal of a pulse sensor coupled to the second fluid containing system. The output signal may indicate individual second pulses or an average time between second pulses. In either case, a predicted time point for a second pulse in the measurement signal can be calculated based on the output signal of the pulse sensor and a known difference in arrival time between the pulse sensor and the pressure sensor(s) that generates the measurement signal(s). The pulse sensor may sense the pressure waves that are generated in the fluid by second pulse generator, or it may directly reflect the pulse generation process in the second pulse generator, e.g. via a control signal for the second pulse generator or a pulse rate meter mechanically coupled to the second pulse generator. In one application, to be further exemplified below, the second fluid containing system is a blood system of a human, and the pulse generator is a human heart. In such an application, the timing information may be provided by any conventional pulse sensor such as a pulse watch, a pulse oximeter, an electrocardiograph, etc.

Alternatively, the timing information may be obtained based on the relative timing of previously detected second pulses in the measurement signal, e.g. given by the time points associated with previously calculated evaluation parameter values. For example, the time difference between the two most recently detected second pulses may be used to predict the time point for subsequent second pulse(s).

Alternatively, the timing information may be obtained from one or more reference signals originating from a reference pressure sensor in the first system. Such a reference pressure sensor is suitably arranged to detect second pulses even if the fluid connection is compromised, e.g. via a second fluid connection between the first and second fluid containing systems.

An example of such a reference pressure sensor is an arterial pressure sensor in an extracorporeal blood flow circuit, to be further described below. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient. The reference signal may be processed for detection of at least one second pulse, using any suitable technique, including the time domain techniques disclosed herein. The time point of the detected second pulse in the reference signal can then be converted to a predicted time point in the measurement signal/filtered measurement signal/evaluation segment using a known/measured difference in pulse arrival/transit time between the reference sensor and the pressure sensor(s) used for monitoring. Thus, in one embodiment, the difference in transit time is given by a fixed and predefined value.

In another embodiment, the difference in transit time between a blood line on the arterial side and a blood line on the venous side in the extracorporeal blood flow circuit is determined based on the actual arterial and venous pressures (absolute, relative, or average), which may be derived from any suitable sensor in the extracorporeal blood flow circuit (including the venous and arterial pressure sensors). The transit time decreases if the pressure increases, i.e., high pressure equals short transit time. During operation of the extracorporeal blood flow circuit, the venous pressure should be higher than the arterial pressure, and thus the transit time should be shorter in the venous blood line compared to the transit time in the arterial blood line. The difference in transit time may be determined based on, e.g., a physical model or a look-up table. The model/table may not only include information about pressure (absolute, relative, or average), but also information about material (elasticity, plasticity, etc.), geometry (length, diameter, wall thickness, etc.), temperature (both fluids and ambient temperature), mechanical factors (clamp, tension, actuators, kinking/occlusion, etc.), fluid properties (viscosity, water/blood, chemical composition, etc.), etc. The thus-determined difference in transit time may then be used to relate a time point of a detected second pulse in the reference signal from the arterial pressure sensor to a predicted time point in the measurement signal/filtered measurement signal/evaluation segment originating from the venous pressure sensor.

In a variant, an improved estimation of the timing information may be obtained by aligning and adding the filtered measurement signal/evaluation segment (derived from the venous pressure signal) with a correspondingly filtered reference signal (derived from the arterial pressure signal), to thereby calculate an average time-dependent signal with improved SNR. The aligning may be based on the aforesaid difference in transit time, given by the actual arterial and venous pressures (absolute, relative, or average). By identifying one or more second pulse(s) in the average time-dependent signal, an improved estimation of the timing information is obtained.

Alternatively or additionally, to potentially improve the precision of the timing information, the timing information may be obtained by intermittently stopping the first pulse generator, while identifying at least one second pulse in the reference signal or the measurement signal.

Optionally, the process of obtaining timing information based on an identified second pulse, be it in the reference signal or the measurement signal, may involve validating the identified second pulse (a candidate pulse) against a temporal criterion. Such a temporal criterion may, e.g., indicate an upper limit and/or a lower limit for the time difference between the time point for the candidate pulse and one or more previously identified (and suitably validated) second pulses. These limits may be fixed, or they may be set dynamically in relation to a preceding time difference. Any candidate pulse that violates the temporal criterion may be removed/discarded from use in obtaining the timing information.

In yet another alternative, the timing information is obtained from a measurement signal using an iterative approach. In this iterative approach, the measurement signal is processed to calculate a time-sequence of evaluation parameter values, e.g. based on the first inventive concept. These evaluation parameter values identify a sequence of candidate pulses and associated candidate time points, which is validated against a temporal criterion. Such a temporal criterion may, e.g., indicate an upper limit and/or a lower limit for the time difference between the candidate time points. The temporal criterion may be given by constraints in the second pulse generator 3'. Any candidate time points that violate the temporal criterion may be removed/discarded, and the timing information may be obtained from the remaining time points.

Different validation methods may be used depending on the availability of previous timing information, i.e. information about time points of preceding second pulses. Such previous timing information may be given by any one of the methods described in the foregoing, or resulting from a previous iteration of the iterative approach.

Figure 7:
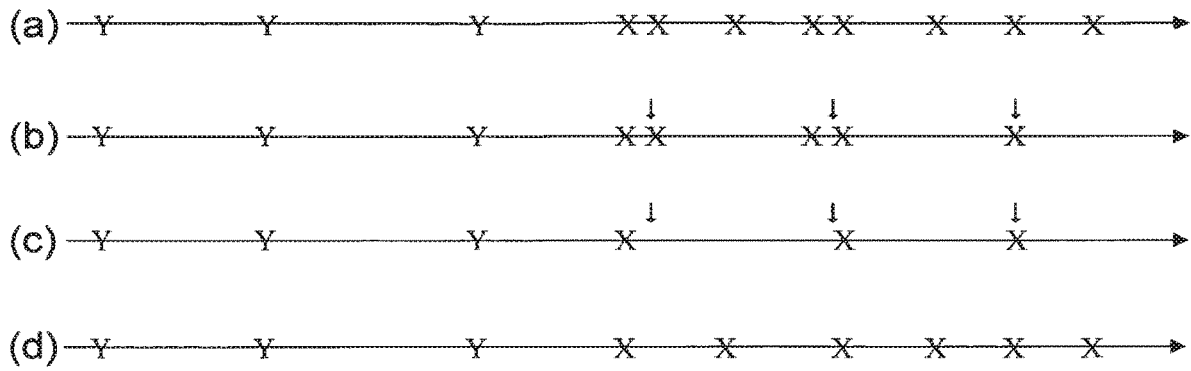
FIGS. 7(a)-7(d) illustrate processing of candidate pulses identified in a measurement signal.

FIG. 7(a) illustrates a sequence of candidate pulses (denoted by X), as well as a sequence of preceding second pulses (denoted by Y), laid out on a time axis. In a first validation step, predicted time points (arrows 1 in FIG. 7(b)) are calculated based on the previous timing information (e.g. second pulses Y). In a second validation step, a first temporal criterion is applied to remove/discard any candidate pulses that lie too far from the predicted time points, as also shown in FIG. 7(b). In a third validation step, a second temporal criterion is applied to retain only the candidate pulse with the largest evaluation parameter value among any candidate pulses that lie too close to each other, as shown in FIG. 7(c).

Figure 8:
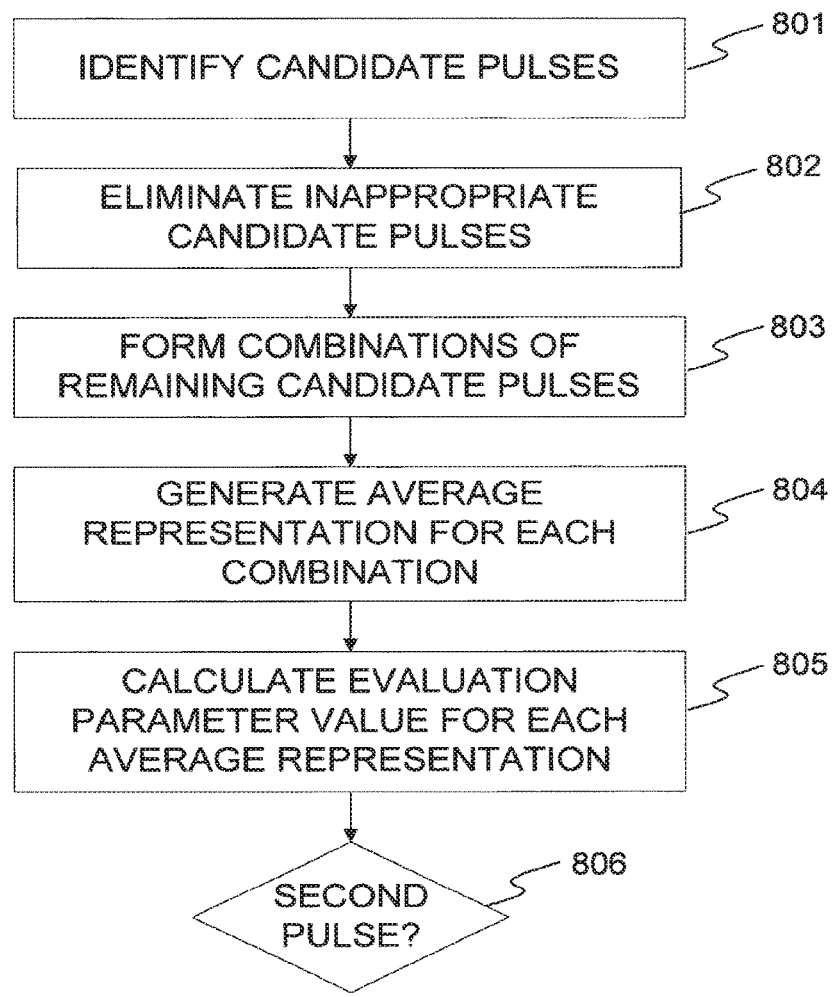
FIG. 8 is a flow chart of part of a monitoring process according to the second inventive concept.

A different validation method may be used if previous timing information is not available. FIG. 8 is a flow chart for such a validation method. The initial step 801 of identifying candidate pulses is followed by a first validation step 802, in which a first temporal criterion is applied to retain only the candidate pulse with the largest evaluation parameter value among any candidate pulses that lie too close to each other. FIG. 7(d) shows an exemplifying result of applying the first validation step 802 to the sequence of candidate pulses in FIG. 7(a). Then, in step 803, different combinations of the remaining candidate pulses are formed. In step 804, an average representation is calculated for each such combination, by aligning and summing corresponding signal segments of the measurement signal/filtered measurement signal. The combinations may be formed based on a second temporal criterion that defines an upper limit and/or a lower limit for the time difference between the candidate pulses. In a second validation step 805, an evaluation parameter value is calculated for each such average representation, and the maximum evaluation parameter value is extracted. Finally, in step 806, it is decided whether the fluid connection is intact or not, by comparing the maximum evaluation parameter value to a threshold value. If the maximum evaluation parameter value exceeds the threshold value, it may be concluded that a second pulse is present and that the fluid connection is intact. It may be noted that there is no need to explicitly extract the timing information in the validation method in FIG. 8, since the use of the timing information is embedded in the final step 806 of determining the integrity of the fluid connection.

It should also be noted that different evaluation parameters and/or threshold values may be used in steps 801 and 806. It is also conceivable to use a combination of two or more of the above alternative methods for obtaining the timing information.

Figure 9:
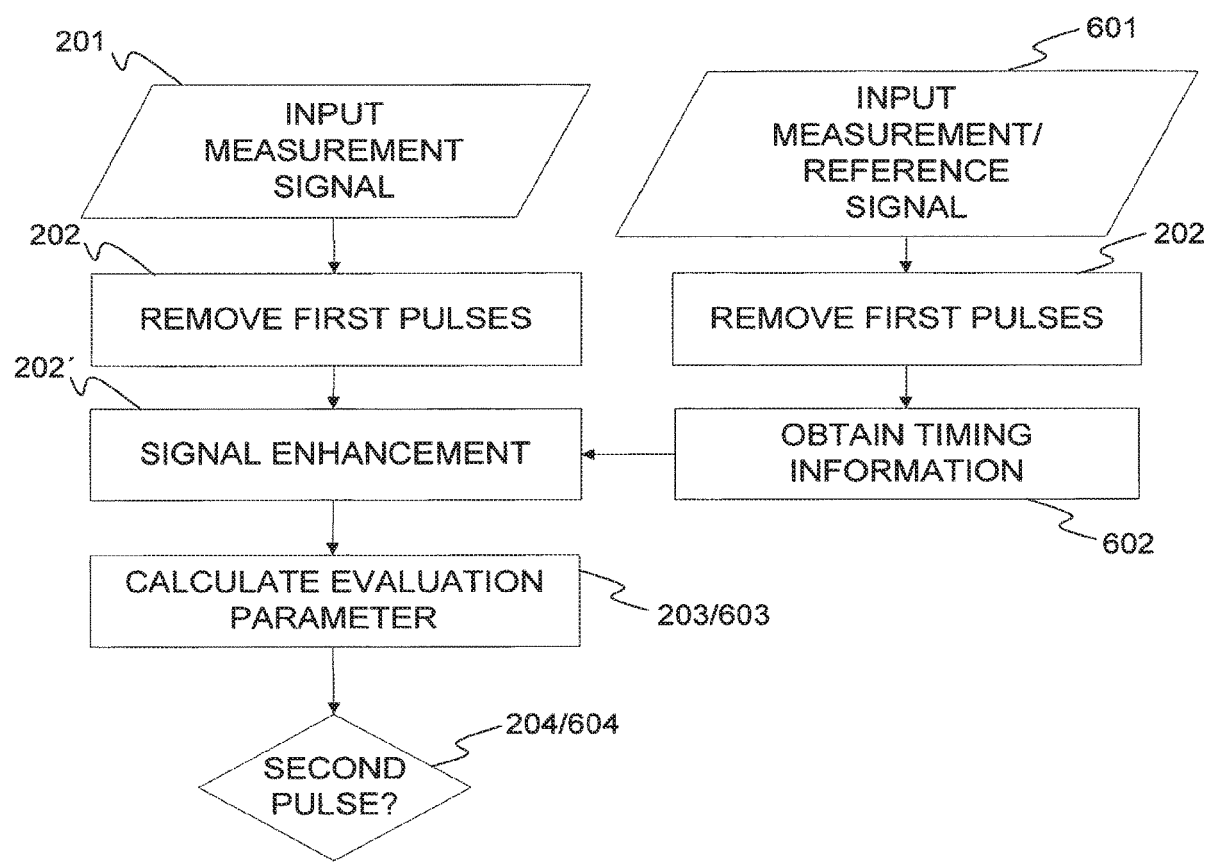
FIG. 9 is a flow chart of a monitoring process that combines the first and second inventive concepts.

FIG. 9 is a flow chart of an embodiment that combines features of the first and second inventive concepts. Specifically, a measurement signal is obtained and filtered according to steps 201 and 202 of the first inventive concept. Then, in step 202', the filtered measurement signal is processed for signal enhancement, based on timing information. As discussed above in relation to FIG. 5, step 202' typically involves identifying, aligning and summing a set of second pulse segments in the filtered measurement signal, to create an average signal representation. An evaluation parameter value is then calculated based on the enhanced signal representation according to step 203/603 of the first/second inventive concept, and it is decided whether the fluid connection is intact or not (steps 204/604). The method also involves receiving a measurement signal (which may be the same measurement signal as in step 201, or the aforesaid reference signal) according to step 601 of the second inventive concept. Then, the measurement/reference signal is filtered to remove the first pulse, if required, according to step 202 of the first inventive concept. Finally, the timing information is obtained according to step 602 of the second inventive concept.

Combinations of Monitoring Techniques

As explained in the foregoing, the technique for monitoring the integrity of the fluid connection can be based on either of the first and second inventive concepts, or a combination thereof. It is also possible to combine such an inventive monitoring technique with one or more conventional monitoring techniques, which e.g. involve the use of an air detector, or a comparison of average pressure levels with threshold values as described by way of introduction. Other conventional monitoring techniques are disclosed in aforesaid WO 97/10013 and US2005/0010118.

It might also be desirable to combine the inventive monitoring techniques with other techniques that are specially designed to handle adverse operating conditions. One such operating condition may arise when the first and second pulses overlap in the frequency domain. As discussed above in relation to step 202 of FIG. 2, such an operating condition could be handled by filtering the measurement signal in the time domain. However, the monitoring precision may be increased further by combining the inventive monitoring technique with a phase-locking technique or a beating detection method, to be described in the following.

The phase-locking technique involves controlling the first/second pulse generator 3, 3' so as to synchronize the pulse rate of the first and second pulse generators 3, 3' while applying a phase difference between the first and second pulses. Thereby, the first and second pulses will be separated in time, and can be detected using the time domain analysis according to the first and/or second inventive concepts. The phase difference may be approximately 180°, since this may maximize the separation of the first and second pulses in the time domain. The phase-locking technique may be activated when it is detected that the frequency of the second pulse generator approaches a frequency of the first pulse generator, or vice versa.

The beating detection method is an alternative or complementary monitoring technique which involves evaluating the presence or absence of a beating signal in the measurement signal to determine the integrity of the fluid connection. The beating signal manifests itself as an amplitude modulation of the measurement signal and is formed by interference between pressure waves generated by the first pulse generator and pressure waves generated by the second pulse generator. Instead of trying to identify second pulses in the measurement signal, the presence of second pulses is identified via the secondary effect of beating. Generally, beating is a phenomenon which is especially noticeable when two signals with closely spaced frequencies are added together. Thus, the beating signal detection is inherently well-suited to be used when the first and second pulses are closely spaced in the frequency domain. The beating signal may or may not be detected by analysing the measurement signal in the time domain. Suitably, the beating detection involves obtaining one or more specific frequencies related to the first pulse generator, and creating at least one filtered measurement signal in which all but one of said specific frequencies are removed. The beating signal may then be detected by determining an envelope of the filtered measurement signal. The beating detection method is the subject of Applicant's co-pending Swedish patent application No. 0800890-6 and U.S. provisional patent application No. 61/045,642, both filed on Apr. 17, 2008.

It is to be understood that in any one of the above combinations, the different monitoring techniques may be carried out in series, in any order, or in parallel.

Performance Improvements

The performance of the different methods for monitoring the integrity of a fluid connection as described herein may be improved by applying any of the following variations.

Hypothesis Test

The determination of the integrity of the fluid connection between the first and second fluid containing systems could be represented by a hypothesis test. In this hypothesis test, the above-mentioned evaluation parameter value $\beta$ is compared to a threshold. The output of the hypothesis is a decision, which may be "intact fluid connection" ($H_1$) if $\beta > \gamma_1$, "compromised fluid connection" ($H_0$) if $\beta > \gamma_0$, or "uncertain decision" if $\gamma_0 \leq \beta \leq \gamma_1$, wherein $\gamma_0$ and $\gamma_1$ are different thresholds.

Magnitude Dependent Monitoring Technique

The monitoring technique may be dynamically adjusted based on the magnitude of the first and/or second pulses in the measurement signal and/or in the reference signal. The dynamic adjustment may affect the process for obtaining timing information and/or the process for obtaining the parameter value based on the measurement signal.

For example, if the magnitude (e.g. amplitude) of second pulses in the reference signal are found to be smaller than the magnitude (e.g. amplitude) of second pulses in the measurement signal, or smaller than a predetermined absolute limit, the timing information may be obtained based on the measurement signal, whereas the timing information otherwise is obtained based on the reference signal (or vice versa). Thus, with reference to FIG. 9, step 601 is adjusted based on the magnitude of second pulses.

In another example, if the magnitude (amplitude) of the second pulses in the reference signal again are found to be too small, the monitoring method may switch to another method for detecting presence or absence of second pulses in the measurement signal, e.g. a method that operates without timing information (e.g. by omitting steps 601, 602, 202 and 202' in FIG. 9).

In the above examples, if the magnitude of first and second pulses are covariant entities, the dynamic adjustment may alternatively be based on the magnitude of first pulses, or the magnitude of a combination of first and second pulses.

Monitoring Technique Based on Patient Data Records

When the second fluid containing system (S2 in FIG. 1) is a blood system of a patient, the monitoring method may be configured to access and use patient-specific information, i.e. existing data records for the patient, e.g. obtained in earlier treatments of the same patient. The patient-specific information may be stored in an internal memory of the surveillance device (25 in FIG. 1), on an external memory which is made accessible to the surveillance device, or on a patient card where the information is e.g. transmitted wirelessly to the surveillance device, e.g. by RFID (Radio Frequency IDentification). For example, the surveillance device may compare the filtered measurement signal, or a parameter derived therefrom, to the patient-specific information. If large differences are identified, a warning may be issued and/or the monitoring technique may be modified (or chosen according to a predetermined table). Furthermore, the patient-specific information may be used by the surveillance device to optimize the monitoring technique by e.g. determining personal threshold values for use in the foregoing algorithms/processes. The patient-specific information may also be used by the surveillance device to determine if an alternative monitoring technique or combinations of monitoring techniques should be used.

Use of Information from Regular Stops of First Pulse Generator

In one embodiment, the first pulse generator is regularly (intermittently or periodically) stopped, and the measurement signal and/or reference signal is analysed for determination of amplitude, frequency and phase of second pulses. This resulting information may then be used to achieve detection by the above-mentioned phase-locking technique. Alternatively or additionally, if the magnitude (e.g. amplitude) of the second pulse(s) detected during such a stop is smaller than a certain limit (chosen with a margin for safe detection), an alert on "uncertain detection" may be issued. Alternatively, if the magnitude is smaller than another limit, the first pulse generator may be actively controlled to be stopped at specific time intervals, where the information obtained during each stop may be used to modify the monitoring technique. For example, the thus-obtained information may be used to change (or add) threshold values in the foregoing algorithms/processes, or to determine if an alternative monitoring technique or combinations of monitoring techniques should be used. In another example, if the thus-obtained information indicates the pulse rate of second pulses, a dedicated bandpass filter (e.g. centered on the thus-obtained pulse rate) may be operated on the measurement signal/filtered measurement signal/evaluation segment to further improve the input to the process for obtaining timing information (cf. step 602 in FIG. 6) and/or the process for obtaining the parameter value based on the measurement signal (cf. step 203/603 in FIGS. 2 and 9). In one embodiment, such a bandpass filter is applied if the rates of first and second pulses are found to differ by more than a certain limit, e.g. about 10%.

In another embodiment, the first pulse generator is selectively controlled so as to reduce the flow rate through the fluid arrangement. By reducing the flow rate, it is possible to accept a longer response time of the monitoring process to a fault condition, while such a longer response time may serve to improve the precision of the monitoring process in detecting fault conditions.

Monitoring of an Extracorporeal Blood Flow Circuit

In the following, for the purpose of illustration only, an implementation of the first and second inventive concepts for monitoring the integrity of a fluid connection is described in the context of extracorporeal blood treatment. The following example involves a combination with the above-mentioned beating detection method. This is only an example, and the monitoring process could be equally implemented without the beating detection method and/or in combination with any one of the other monitoring techniques discussed above.

It should also be understood that the following implementation of the first and second inventive concepts, as well as the beating detection method, is not limited to extracorporeal blood treatment, but is generally applicable for monitoring the integrity of a fluid connection between first and second fluid containing systems.

Figure 10:
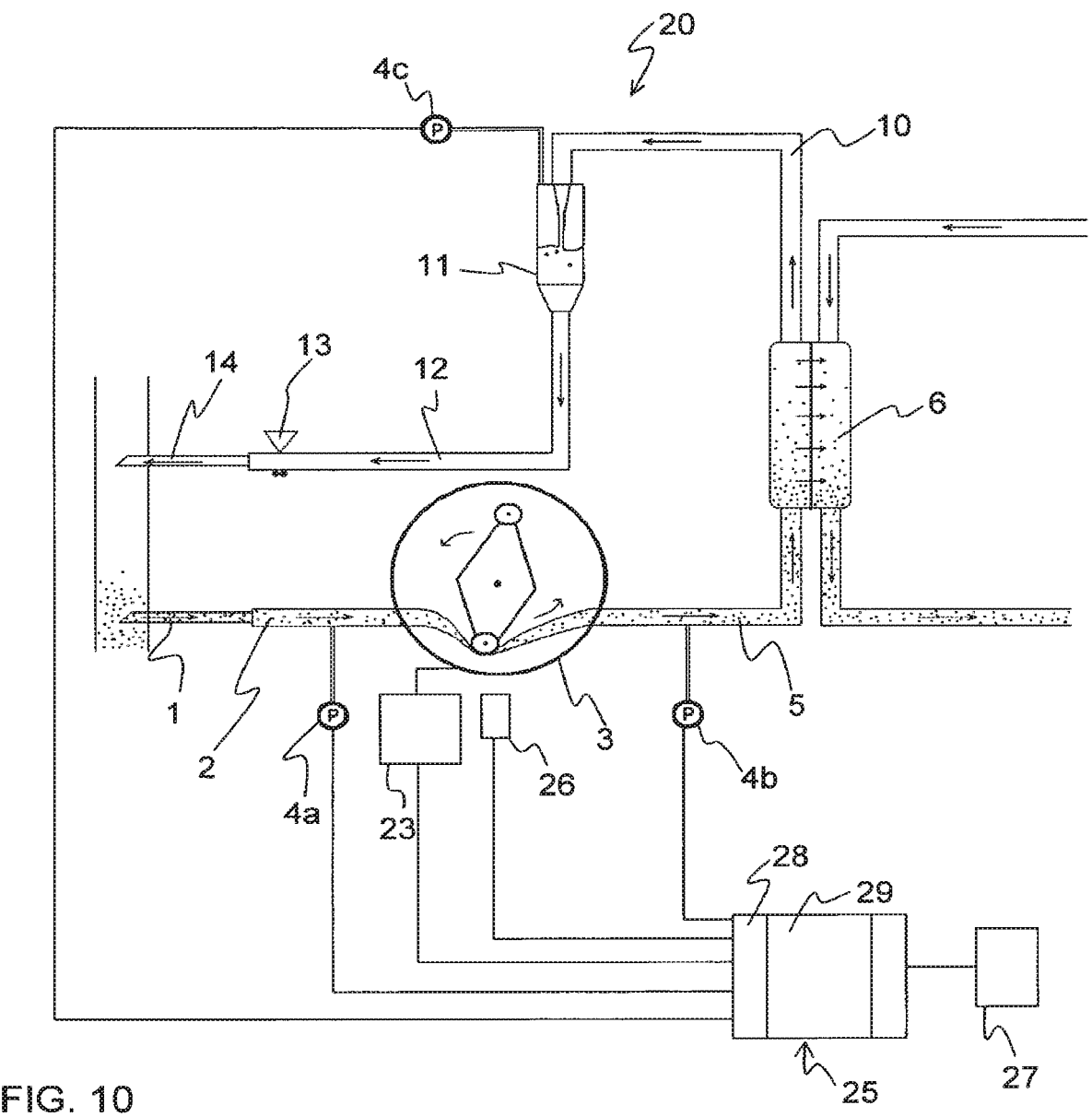
FIG. 10 is a schematic view of a system for hemodialysis treatment including an extracorporeal blood flow circuit.

FIG. 10 shows an example of an extracorporeal blood flow circuit 20 of the type which is used for dialysis. The extracorporeal blood flow circuit 20 comprises components 1-14 to be described in the following. Thus, the extracorporeal blood flow circuit 20 comprises an access device for blood extraction in the form of an arterial needle 1, and an arterial tube segment 2 which connects the arterial needle 1 to a blood pump 3 which may be of peristaltic type, as indicated in FIG. 10. At the inlet of the pump there is a pressure sensor 4a (hereafter referred to as arterial sensor) which measures the pressure before the pump in the arterial tube segment 2. The blood pump 3 forces the blood, via a tube segment 5, to the blood-side of a dialyser 6. Many dialysis machines are additionally provided with a pressure sensor 4b that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4c (hereafter referred to as venous sensor) is provided to measure the pressure on the venous side of the dialyser 6. In the illustrated example, the pressure sensor 4c measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

As discussed by way of introduction, it may be vital to monitor the integrity of the fluid connection to the blood vessel access with respect to malfunction in the injection and/or extraction of blood therethrough. In many dialysis machines, one or more of said pressure detectors 4a-4c are not present. However, there will be at least one venous pressure sensor. The following description is focused on monitoring the integrity of the fluid connection between the blood vessel access and the venous needle based on a measurement signal from the venous pressure sensor. The monitoring process involves a so-called direct detection method, which may implement one of the first and second inventive concepts, and its different embodiments, as discussed above. Thus, in relation to the general arrangement in FIG. 1, the extracorporeal blood flow circuit 20 corresponds to the first fluid containing system S1, the blood pump 3 (as well as any further pulse source(s) within or associated with the extracorporeal blood flow circuit 20, such as a dialysis solution pump, valves, etc.) corresponds to the first pulse generator 3, the blood system of the patient corresponds to the second fluid containing system S2, and the heart of the patient corresponds to the second pulse generator 3'.

In FIG. 10, a control unit 23 is provided, i.a., to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

Further, in FIG. 10, a surveillance/monitoring device 25 is configured to monitor the integrity of the venous-side fluid connection between the patient and the extracorporeal blood flow circuit 20, specifically by monitoring the presence of a signal component originating from the patient's heart in a blood pressure signal. Absence of such a signal component is taken as an indication of a failure in the integrity of the fluid connection, and brings the device 25 to activate an alarm and/or stop the blood flow, e.g. by stopping the blood pump 3 and activating a clamping device 13 on tube segment 12. The surveillance device 25 is at least connected to receive a measurement signal of the pressure sensor 4c. The device 25 may also be connected to pressure sensors 4a, 4b, as well as any additional pressure sensors included in the extracorporeal blood flow circuit 20. As indicated in FIG. 10, the device 25 may also be connected to the control unit 23. Alternatively or additionally, the device 25 may be connected to a measurement device 26 for indicating the frequency and phase of the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of a dialysis apparatus.

In FIG. 10, the surveillance device 25 comprises a data acquisition part 28 for pre-processing the incoming signal(s), e.g. including an A/D converter with a required minimum sampling rate and resolution, one or more signal amplifiers, one or more filters to remove undesired components of the incoming signal(s), such as offset, high frequency noise and supply voltage disturbances.

In the examples given herein, the data acquisition part 28 comprises a DAQ card USB-6210 from National Instruments with a sampling rate of 1 kHz and resolution of 16 bits, an operation amplifying circuit AD620 from Analog Devices, a high-pass filter with a cut-off frequency of 0.03 Hz (i.a., for removal of signal offset) together with a low-pass filter with a cut-off frequency of 402 Hz (i.a., for removal of high frequency noise). To obtain a short convergence time, a low-order filter is used for the high-pass filter. Furthermore, the data acquisition part 28 may include an additional fixed band-pass filter with upper and lower cut-off frequencies of 0.5 Hz and 2.7 Hz, respectively, which corresponds to heart pulse rates between 30 and 160 beats per minute. This filter may be used to suppress disturbances outside the frequency interval of interest.

After the pre-processing in the data acquisition part 28, the signal from the pressure sensor 4c is provided as input to a data analysis part 29, which executes the actual monitoring process. FIG. 11(a) shows an example of such a pre-processed pressure signal in the time domain, and FIG. 11(b) shows the corresponding power spectrum, i.e. the pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pumping frequency in the following, is the frequency of the pump strokes that generate pressure waves in the extracorporeal blood flow circuit. For example, in a peristaltic pump of the type shown in FIG. 10, two pump strokes are generated for each full revolution of the rotor. FIG. 11(b) also indicates the presence of a frequency component at half the pumping frequency ($0.5f_0$) and harmonics thereof, in this example at least $f_0$, $1.5f_0$, $2f_0$ and $2.5f_0$. FIG. 11(b) also shows a heart signal (at 1.1 Hz) which in this example is approximately 40 times weaker than the blood pump signal at the base frequency $f_0$.

Figure 12:
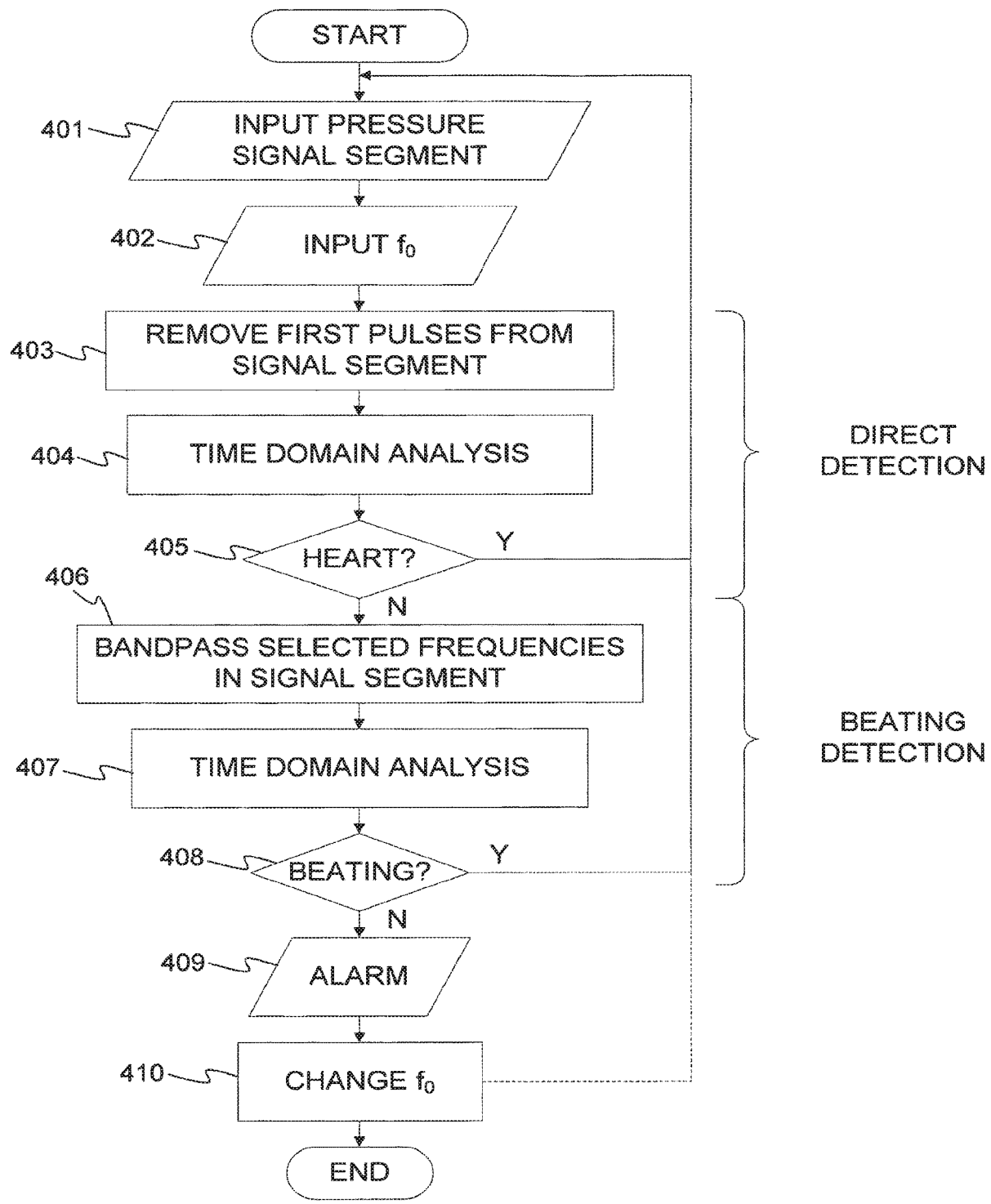
FIG. 12 is a flow chart of an exemplifying monitoring process.

FIG. 12 is a flow chart for a data analysis or monitoring process according to an embodiment of the present invention. The illustrated process implements a combination of detection methods to monitor the integrity of the fluid connection between the extracorporeal blood flow circuit 20 and the blood system of a human. One detection method ("direct detection") involves using a time domain analysis for detecting a heart pulse in the pressure signal. Another detection method ("beating detection") involves detecting an amplitude modulation (beating signal) in the pressure signal, the amplitude modulation being caused by interference between pressure waves originating from the patient's heart and the blood pump. These detection methods will be described in further detail below, but first the overall operation of the process will be briefly outlined.

The monitoring process starts by inputting a signal segment of the pressure signal (step 401), as well as information on the base frequency ($f_0$) of the blood pump (step 402). This frequency information may be obtained from processing of the pressure signal itself. Alternatively, it may be obtained from a signal generated by a dedicated measurement device (cf. 26 in FIG. 10), or from a signal indicative of a set value or actual value used by the control unit (cf. 23 in FIG. 10). It is to be understood that step 402 need not be executed for every iteration of the monitoring process.

Figure 11:
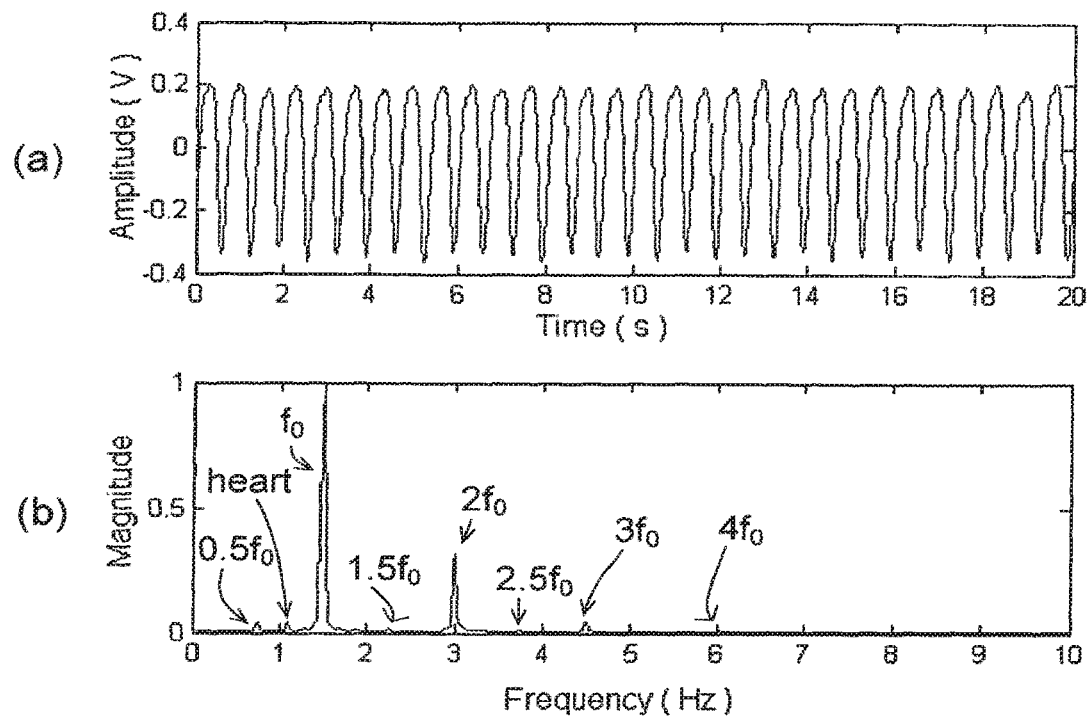
FIG. 11(a) is a plot in the time domain of a venous pressure signal containing both pump frequency components and a heart signal.
FIG. 11(b) is a plot of the corresponding signal in the frequency domain.

The direct detection method involves steps 403-405, in which the signal segment is processed so as to remove first pulses originating from the blood pump, e.g. by blocking one or more of the frequency components (see $0.5f_0$, $f_0$, $1.5f_0$, $2f_0$, $2.5f_0$, $3f_0$ and $4f_0$ in FIG. 11) related to the blood pump. Typically, step 403 (corresponding to step 202 in FIG. 2) is designed to effectively "clean" the signal segment from all frequency components emanating from the blood pump. In step 404 (corresponding to step 203 in FIG. 2), the signal segment is analysed in the time domain to identify any remaining signal pulse emanating from the patient's heart. If such a heart pulse is detected in step 405 (corresponding to step 204 in FIG. 2), the monitoring is returned to step 401, in which a new pressure signal segment is inputted for processing. As mentioned above, this new signal segment may or may not partially overlap the preceding signal segment. If no heart component is detected in step 405, the monitoring proceeds to beating detection. The lack of a heart pulse may result from a malfunction of the venous-side fluid connection, e.g. by the venous needle detaching from the blood vessel access, or by the heart pulse being too weak to be detected. Alternatively, the heart beat frequency may essentially coincide with any of the frequency components of the blood pump, causing the heart pulse to be accidentally eliminated in the filtering step 403.

In an alternative implementation, the direct detection method steps 403-405 correspond to steps 602-604 according to the second inventive concept discussed above in relation to FIG. 6.

In either implementation, the direct detection method may utilize timing information, which may be obtained as described above in relation to the second inventive concept.

The beating detection method involves steps 406-408, in which the signal segment is processed so as to identify a beating signal caused by interference between pressure waves originating from the heart and the blood pump, respectively. The beating signal is perceived as periodic variations in signal amplitude with a frequency equal to the difference in frequency between these two pressure waves. Thus, instead of searching for the heart pulse itself in the pressure signal, the beating detection looks at indirect effects of the heart pulse on the pressure signal in the time domain.

In step 406, the signal segment is processed to remove all frequencies except for one or more selected frequency bands. Each such selected frequency band is a band surrounding only one of the frequency components (see $0.5f_0$, $f_0$, $1.5f_0$, $2f_0$, $2.5f_0$, $3f_0$ and $4f_0$ in FIG. 11) related to the blood pump. This selective bandpass filtering may be effected to facilitate the detection of the beating signal. The pressure wave from the heart is generally much smaller (typically 20-200 times) than the pressure wave from the blood pump, so a potential beating wave will be weak and possibly difficult to detect. Typically, all frequencies outside one such selected frequency band are removed from the signal segment, whereupon the resulting filtered signal segment is analysed in the time domain for detection of a beating signal (step 407). If the blood pump is known to produce a number of frequency components (as shown in FIG. 11), step 406 results in a set of filtered signal segments, each including only frequencies around one of these frequency components. These filtered signal segments may be generated in parallel and then analysed in step 407. Alternatively, filtered signal segments may be generated in sequence, based on a given order of blood pump frequency components. Each filtered signal segment may be passed on to step 407 for analysis before another filtered signal segment is generated, such that the generating of filtered signal segments is interrupted as soon as a beating signal is detected.

In yet another embodiment, the heart pulse rate is known. In such a situation, step 406 may be limited to generating only one filtered signal segment, which includes only frequencies around the frequency component that lies closest to the known heart frequency. The heart pulse rate is suitably obtained in similar way as the timing information.

The selective bandpass filtering of step 406 may use a fixed width of the frequency band(s), which is set in view of a desired performance of the beating detection method, typically the maximum frequency spacing between a heart pulse and a pump frequency component that should result in a beating signal. For example, the frequency bands used by the beating detection method may be small compared to the spacing of the pump frequency components, if the beating detection method is used in combination with another detection method (e.g. the direct detection method) which is capable of detecting presence/absence of a heart signal in specific frequency regions in between these frequency components. In other situations, the frequency bands may have about the same total width as the spacing of the pump frequency components, or the frequency bands of adjacent pump frequency components may even overlap. In another embodiment, the width of the frequency band(s) may be adaptively set as a function of a previously determined heart frequency. For example, the width may be reduced as the heart frequency approaches one of the pump frequency components. As mentioned above, the heart frequency may e.g. be obtained from a separate pulse rate meter, another pressure sensor, or in a preceding iteration of the monitoring process.

However, it is to be understood that the selective bandpass filtering around different frequency components of the blood pump is included to facilitate beating detection, but may be dispensed with.

If a beating signal is detected in step 408, the monitoring is returned to step 401, in which a new pressure signal segment is inputted for processing. If no beating signal is detected in step 408, the monitoring proceeds to activate an alarm that indicates a malfunction, or at least a warning that such a malfunction may have occurred (step 409). Concurrently with activating the alarm/warning, the process may proceed to step 410 in which the pumping frequency is changed, whereupon the monitoring process may return to step 401 to continue to monitor the integrity of the fluid connection between the blood vessel access and the venous needle. If a heart component/beating signal is discovered during subsequent iteration(s) of the monitoring process, the alarm/warning may be shut off. Alternatively, to minimize the number of false alarms, the alarm/warning may be activated only if the monitoring process fails to detect the heart signal both before and after such a change in pumping frequency.

In one embodiment of step 410, the pump is kept operative, but its pumping frequency is changed. In one variant, the pumping frequency is lowered in order to reduce the blood flow and thereby minimize any blood loss caused by the potential malfunction that has been detected. In another variant, the pumping frequency is actively shifted such that its frequency components are non-coincident with its previous frequency components. For example, the base frequency could be shifted by a fraction of the spacing between the frequency components originating from the pump. In the example of FIG. 11, this would mean a fraction of $0.5f_0$. Typically, the shift represents a reduction in the pumping frequency.

In another embodiment of step 410, the pump is shut-down (i.e. $f_0=0$) to remove the interference from the blood pump while also minimizing any blood loss caused by the potential malfunction that has been detected. In a variant of such an embodiment, step 410 also involves identifying the frequency of the heart while the blood pump is shut-down, and then re-starting the blood pump with a pumping frequency shifted from the thus-identified heart frequency. The heart frequency may be identified from the pressure signal, e.g. using the spectral signal analysis of step 404.

Figure 13:
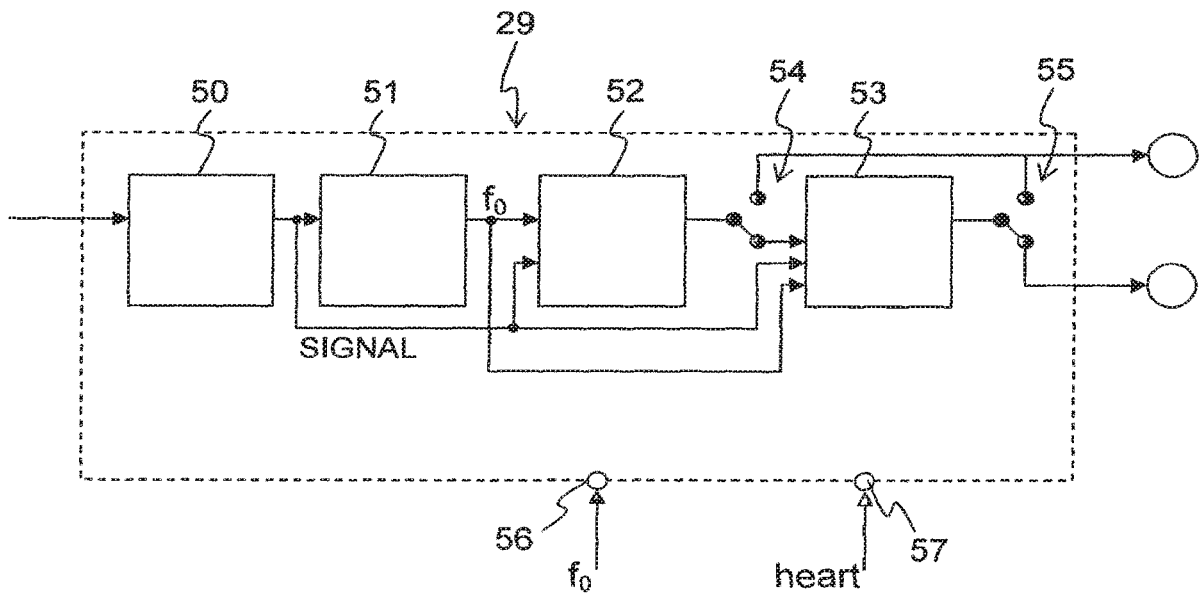
FIG. 13 is a block diagram of a data analyser for executing the process of FIG. 12.

FIG. 13 is a block diagram of the data analysis part (cf. 29 in FIG. 10) which is configured to carry out the monitoring process shown in FIG. 12. In the illustrated embodiment, the data analysis part includes a storage block 50, a pump frequency determination block 51, a direct detection block 52, a beating detection block 53, and switching blocks 54, 55 for connecting the output of the direct detection block 52 and the beating detection block 53 to an alarm device. Although not shown, a control block may be provided to synchronize the operation of the blocks 50-55.

The data analysis part 29 may be implemented by software running on a processing device, such as a general- or special-purpose computer device or a programmed microprocessor. The storage block 50 may be a volatile or non-volatile memory of such a computer device, whereas the other blocks 51-55 may be implemented by software instructions. However, it is conceivable that some or all blocks are fully or partially implemented by dedicated hardware, such as an FPGA, an ASIC, or an assembly of discrete electronic components (resistors, capacitors, operational amplifier, transistors, etc), as is well-known in the art.

The storage block 50 is operated to store the incoming pressure signal as a sequence of data samples. The other blocks 51-53 are then operated to receive or retrieve segments of the stored pressure signal from the storage block 50. The storage block 50 thus buffers the incoming pressure signal, allowing overlapping or non-overlapping signal segments to be individually processed and analysed. The storage block 50 may, e.g., be implemented as a plurality of linear buffers or as a circular buffer.

Block 51 is configured to determine the frequency of the blood pump based on a signal segment. An example of an algorithm used by such a block will be further described below.

Block 52 implements the direct detection steps 403-405 (FIG. 12), based on an estimated pumping frequency provided by the pump frequency determination block 51. If the outcome of the determination step 405 is negative, i.e. no heart component is found, switching block 54 is operated to activate block 53. If a heart component is found, switching block 54 may be operated to provide a positive status indication to the alarm device, and a new signal segment may be received or retrieved by blocks 51, 52.

Block 53 implements the beating detection steps 406-408 (FIG. 12), again based on the estimated pumping frequency. If the outcome of determination step 408 is negative, i.e. no beating signal is detected, switching block 55 is operated to provide a negative status indication to the alarm device, which issues an alarm. If a beating signal is found, switching block 55 may be operated to provide a positive status indication to the alarm device, and a new signal segment may be received or retrieved by the blocks 51, 52.

In FIG. 13, the data analysis part also includes an input 56 for receiving a signal indicative of the pumping frequency (e.g. from the measurement device 26 or the control unit 23 in FIG. 10). As discussed in relation to step 410 (FIG. 12), frequency information obtained from this signal may supplement or replace the frequency determined by block 51.

FIG. 13 also indicates the provision of an input 57 for a measurement signal indicative of the patient's heart frequency, e.g. to provide timing information to block 52 or to be used by block 53 when executing step 406.

An exemplifying operation for each of the blocks 51-53 will now be described, starting with the pump frequency determination block 51.

The pump frequency determination block 51 is configured to calculate a power spectrum from a pressure signal segment, and identify the base pumping frequency in the power spectrum. The power spectrum can be calculated in any known way, e.g. by operating a DFT (Discrete Fourier Transform) or an FFT (Fast Fourier Transform) on the pressure signal segment. The base pumping frequency may be identified as the frequency of the largest peak in the power spectrum, or at least among one of the largest peaks.

If the resolution of the power spectrum is low, special measures may be employed to increase the accuracy of the estimated frequency. The resolution is dependent on the sampling frequency $f_s$ and the number of samples N in the signal segment as $f_s/N$. In one example, signal segments of 20 seconds are sampled at 10 Hz, with a resolution of 0.05 Hz. This accuracy may be inadequate for the processing in the direct detection block 52 and/or beating detection block 53. To increase the accuracy, the signal segment may be bandpass filtered in a narrow range around the estimated frequency obtained from the power spectrum, resulting in a comparatively noiseless and sinusoid-like signal segment. A precise estimation of the base frequency can then be obtained by determining the period of the filtered signal segment in the time domain, e.g. by adapting a sinusoid to the filtered signal and identifying the time difference between zero-crossings.

The direct detection block 52 may comprise components for cancelling the signal pulses that emanate from the blood pump, and any further interfering pulse sources (i.e. the "first pulses" discussed above in relation to the first and second inventive concepts). Furthermore, the direct detection block 52 may comprise components that obtain the aforesaid timing information, as well as components that carry out the time domain analysis according to the first and/or second aspects for identification of heart pulses in the pressure signal.

The beating detection block 53 is configured to filter the signal segment with respect to a set of passbands, each containing one frequency component of the blood pump. Each resulting filtered signal segment is essentially a sinusoid. If the frequency of the heart lies within one of these passbands, then the corresponding filtered signal segment will have a waveform not to be found in any of the other filtered signal segments.

Figure 14:
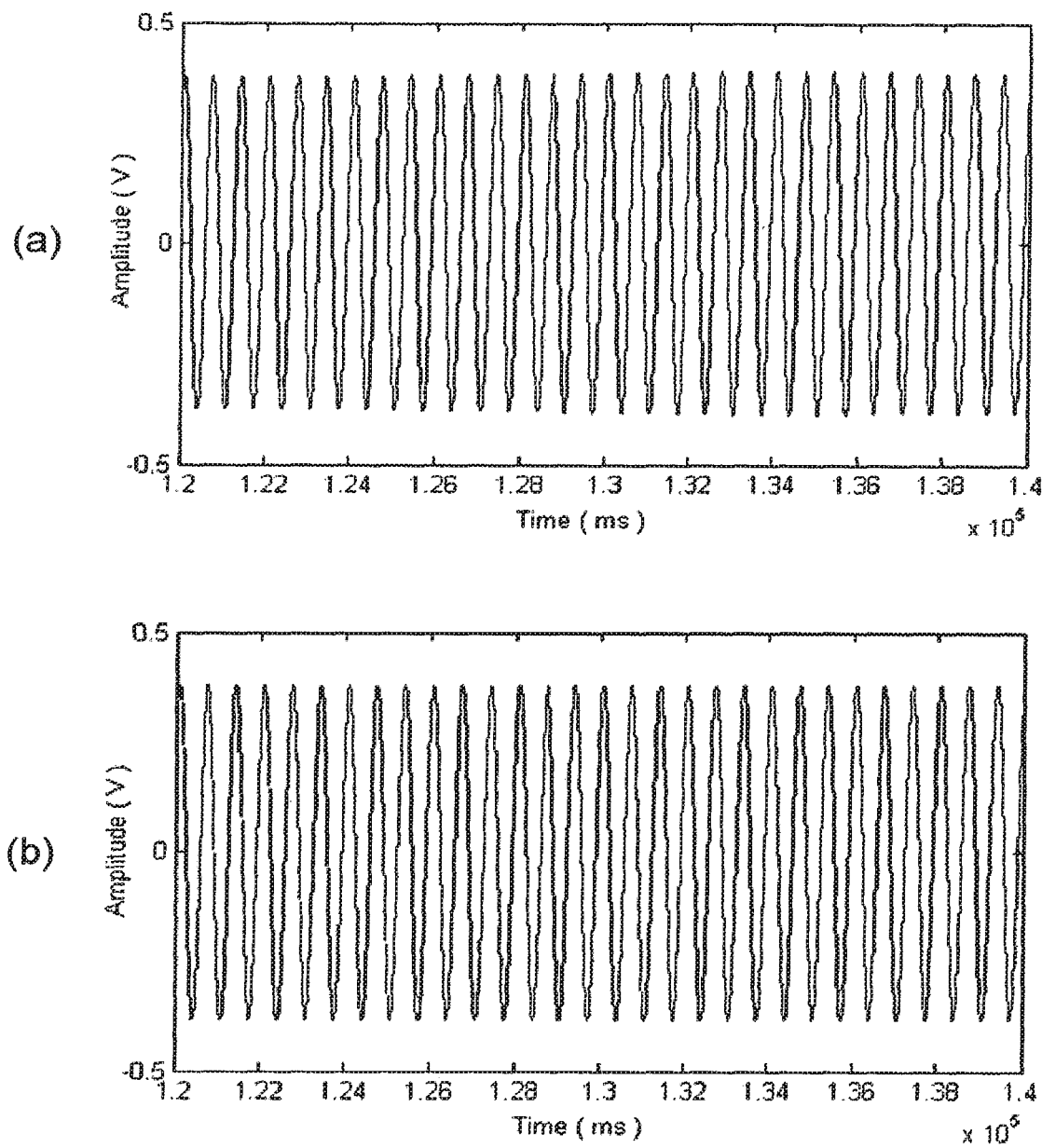
FIGS. 14(a) and 14(b) are plots in the time domain of a pressure signal after processing in a beating detection module in the data analyser of FIG. 13, with and without a heart signal.
Figure 15:
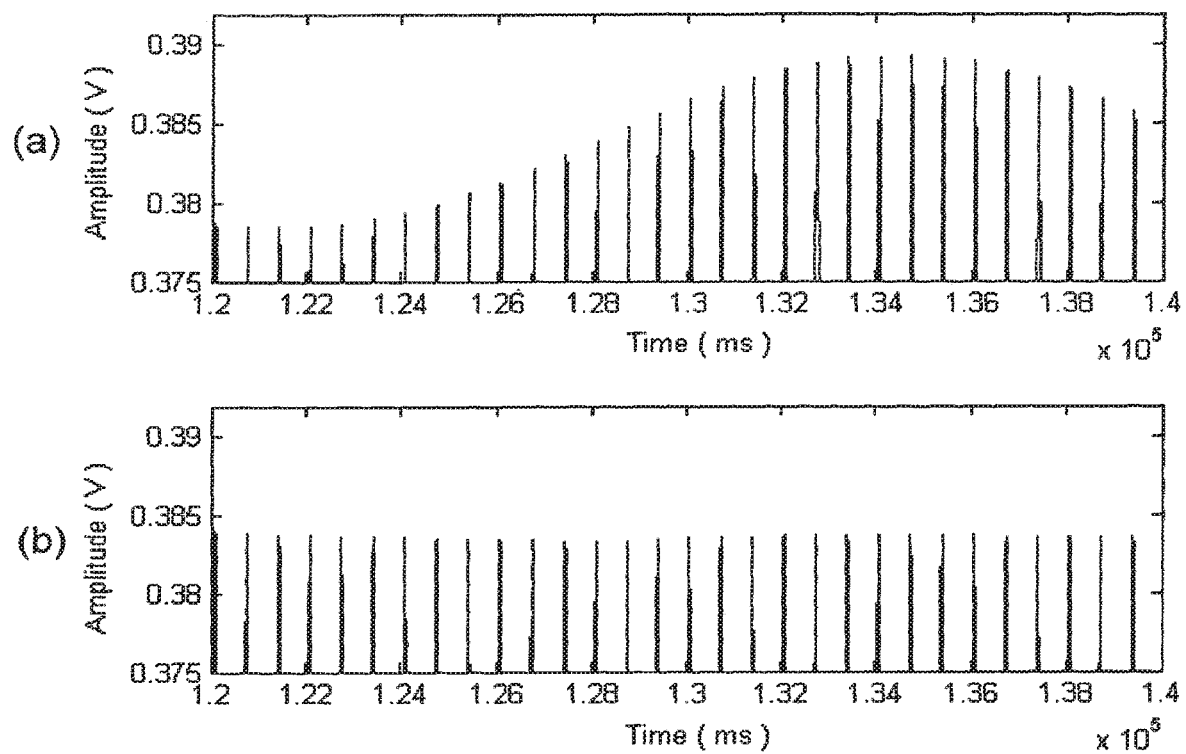
FIGS. 15(a) and 15(b) are enlarged view of the plots in FIGS. 14(a) and 14(b).

FIG. 14(*a*) shows a 20 second signal segment which has been filtered with a narrow bandpass surrounding the base frequency of the blood pump at 1.5029 Hz. The filtered signal also contains a heart pulse, which has a frequency shift of 0.037 Hz with respect to the base frequency. The relative magnitude between the blood pump and heart pulse is 40:1. FIG. 14(*b*) shows a corresponding filtered signal segment without a heart signal. Although being very small, it is possible to distinguish a difference between the signal segments, where the presence of the heart causes an overlying variation in signal amplitude in FIG. 14(*a*) which is lacking in FIG. 14(*b*). FIGS. 15(*a*) and 15(*b*) are enlarged views of the signal peaks in FIGS. 14(*a*) and 14(*b*), respectively, showing a clear difference between the filtered signal segments with and without a heart pulse.

In one embodiment, the beating detection block 53 is configured to detect the beating signal based on an envelope obtained from the filtered signal segment.

Figure 16:
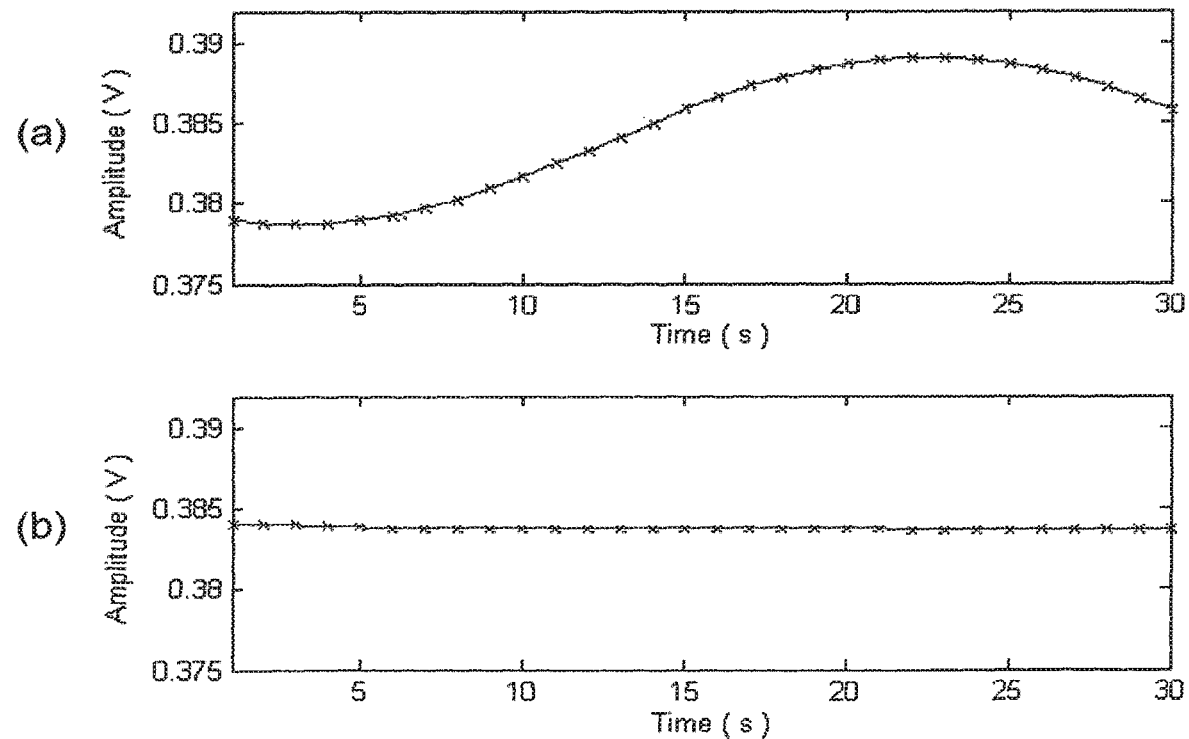
FIGS. 16(a) and 16(b) are plots of envelopes extracted from the data in FIGS. 15(a) and 15(b).

In one such variant, the beating detection block 53 obtains the envelope by extracting an array of peak values from the signal segment. The extracted peak values may be given by extracting signal values of individual peaks identified in the signal segment. To improve noise robustness, each extracted peak value may instead be calculated as an average or sum of the signal values forming each peak in the signal segment, e.g. including signal values within 10-25% of the peak value or within a given time range around the peak value. The obtained envelope (peak value array) is then processed for calculation of an evaluation parameter. FIGS. 16(*a*) and 16(*b*) show peak value arrays extracted from FIGS. 15(*a*) and 15(*b*), respectively.

In another variant, block 53 obtains the envelope by applying a linear, time-invariant filter known as a Hilbert transformer to the signal segment x. This operation results in a transformed signal segment x̌ which is a 90° phase-shifted version of the signal segment. The envelope b̂(n) can then be obtained from $$b(n) = \sqrt{x^2(n) + \check{x}^2(n)},$$

with n being the different positions in the signal segment.

For improved processing efficiency, block 53 may obtain an approximate envelope b(n) from the signal segment x based on the relation $$\hat{b}(n) = |x(n)| + \frac{2}{\pi}|x(n+1) - x(n-1)|.$$

The obtained envelope, be it approximate or not, is then processed for calculation of an evaluation parameter.

In either variant, the obtained envelope may be low-pass filtered to further remove envelope noise, before being processed for calculation of the evaluation parameter.

In either variant, the resulting value of the evaluation parameter may be compared to a threshold value for determining presence or absence of a beating signal.

In one example, the evaluation parameter is the absolute sum of derivatives of the values of the envelope, given by:

$$\sum_{n=0}^{N-1} |(b(n+1) - b(n))|$$

with b(n) being the envelope value at position n, and N being the number of values in the envelope.

Figure 17:
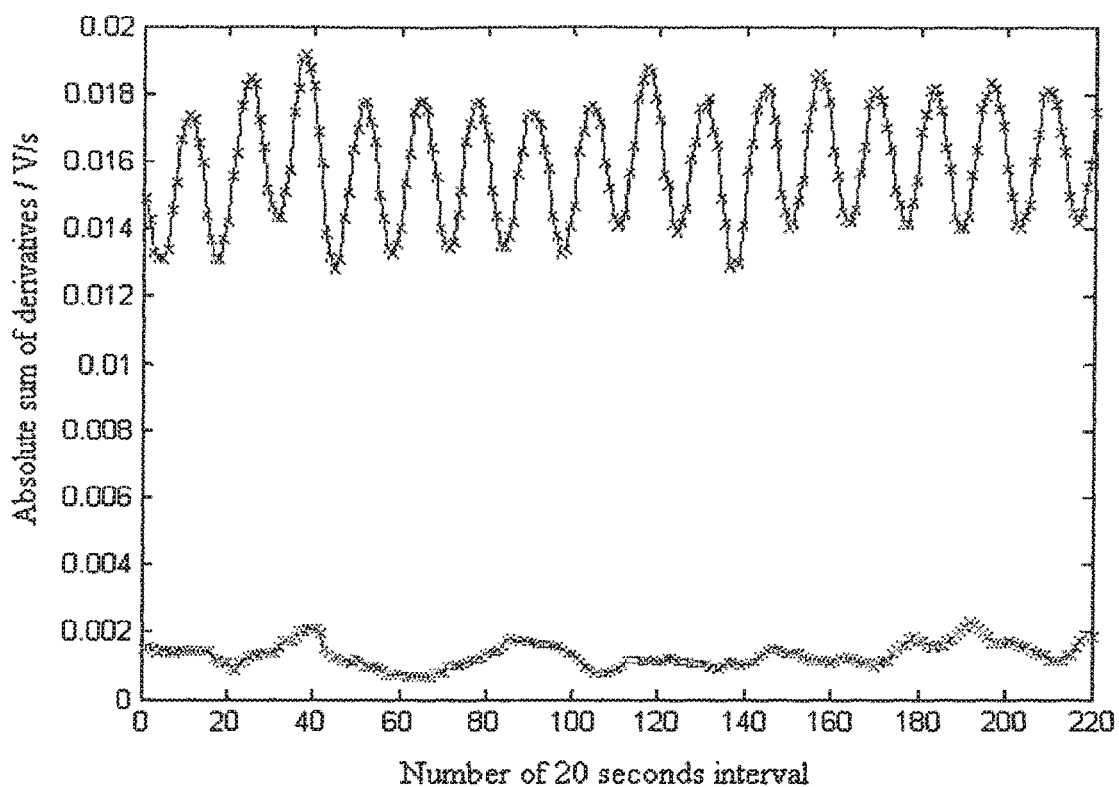
FIG. 17 is a plot of the sum of derivatives as a function of time, calculated from envelopes with and without a heart signal.

FIG. 17 illustrates a result of moving a 20 second window over a 5 minute pressure signal, one second at the time, and calculating the absolute sum of derivatives on an envelope obtained for each 20-second signal segment. The upper curve is calculated for filtered signal segments containing a heart signal, and the lower curve is calculated for filtered signal segments without a heart signal. Clearly, a threshold value can be defined to distinguish between the presence and absence of a heart signal.

The upper curve exhibits a waveform due to the fact that the signal segment contains part of a full beating signal period. Thus, over time, the signal segments will contain different parts of the beating signal. Since the gradient is small around the peaks and valleys of the envelope and larger therebetween, the calculated sum of derivatives will vary correspondingly over time. It should be realized that, for a given length (time window) of the signal segment, the detectability of the gradients will decrease with decreasing frequency difference between heart and blood pump, since this lowers the beating frequency and flattens the envelope. A wider time window will improve the detectability until the point where the amplitude of the beating becomes smaller than the noise.

Figure 18:
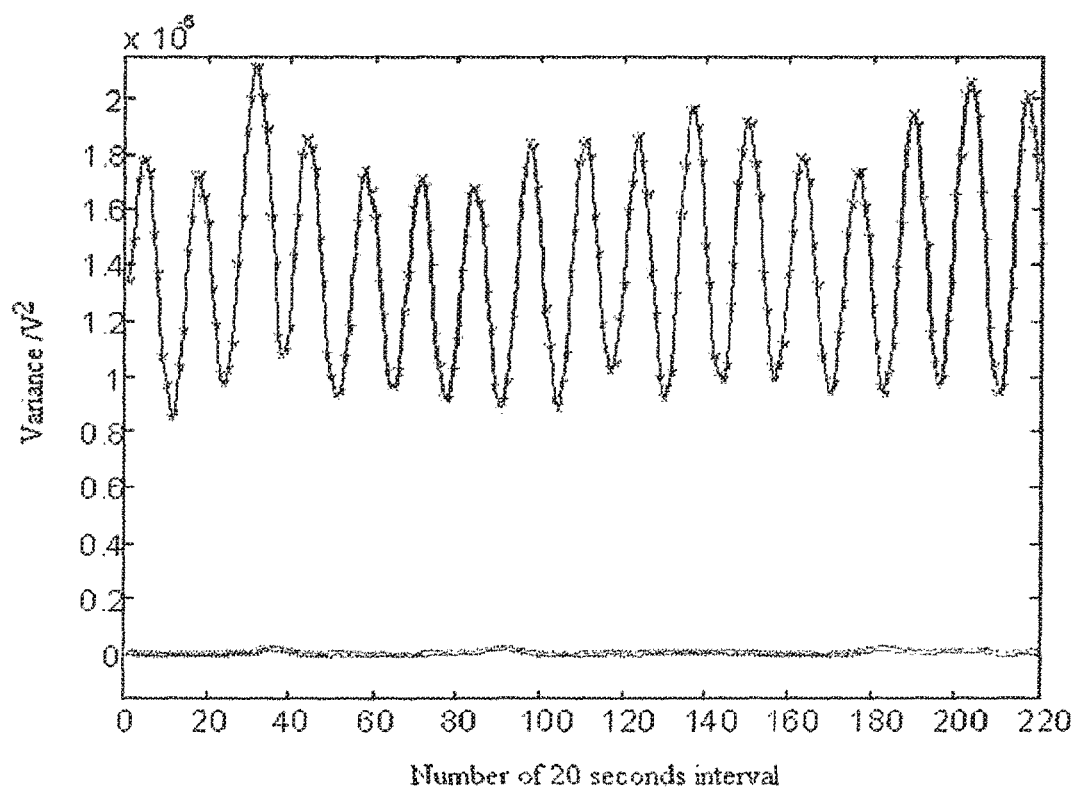
FIG. 18 is a plot of variance as a function of time, calculated from envelopes with and without a heart signal.

In another example, the evaluation parameter is the variance of the values of the envelope. FIG. 18 is a plot corresponding to FIG. 17, but illustrating the variance as a function of time, with (upper) and without (lower) a heart signal. Clearly, a threshold value can be defined to distinguish between the presence and absence of a heart signal.

In yet another example, which may reduce influence of envelope noise, the evaluation parameter is an averaged sum of derivatives, e.g. given by $$\sum_{n=1}^{N-1} \left| \frac{(b(n+1) - b(n-1))}{2} \right|$$

In another embodiment, the beating detection block 53 determines the presence or absence of a beating signal based on pattern recognition processing. For example, all or part of the signal segment or the envelope may be matched against one or more predetermined signal patterns that are representative of a beating signal. In one example, the obtained envelope (optionally low-pass filtered) may be cross-correlated or otherwise convolved with each of a set of sinus waves of different frequencies. Each cross-correlation/convolution results in a correlation curve, from which a maximum correlation value can be obtained. The resulting set of maximum correlation values may then be compared to a threshold value for determining presence/absence of a beating signal, where a high enough maximum correlation value may be taken as an indication of such presence.

In an alternative implementation, the beating detection block 53 operates on signal segments that are long in relation to the period of the beating signal, and processes these signal segments to detect the beating signal in the frequency domain, e.g. by operating a Fourier transformation on the envelope.

All of the above examples of determining presence of a beating signal may involve the further step of assessing the reliability of the determined beating signal. This assessment may involve determining the beating frequency of the beating signal and checking if this beating frequency is reasonable. Depending on how the beating signal is identified, the beating frequency may be determined by processing the obtained envelope in the time/frequency domain, or by identifying the frequency of the sinus wave that yields the maximum correlation value. The beating frequency may be checked in absolute terms and/or in relation to one or more beating frequencies determined in preceding iterations of the monitoring process (FIG. 12), where large enough deviations from the preceding beating frequency/frequencies may be taken as an indication that the determined beating signal is unreliable. The assessment may result in a reliability score that indicates the reliability of the determined beating signal. Alternatively or additionally, the reliability assessment may include the step of controlling the pump to change its pumping frequency and checking if a corresponding change occurs in the beating signal. For example, the pumping frequency may be shifted slightly, or the pump may be intermittently shut-down. The outcome of the reliability assessment may affect the execution of steps 409-410, e.g. whether an alarm/warning is activated, whether further iterations of the monitoring process is required before activating the alarm/warning, whether the pumping frequency is to be changed, etc.

Tests have shown that different evaluation parameters may be preferable in different situations. For example, the use of variance may increase the detectability when looking for a beating signal around one of the harmonics, whereas the use of absolute sum of derivatives or averaged sum of derivatives may be better when looking for a beating signal around the base frequency. Pattern recognition may be resorted to when other detection methods fail. Thus, the beating detection block 53 may be configured to use one or any combination of these evaluation parameters.

Figure 19:
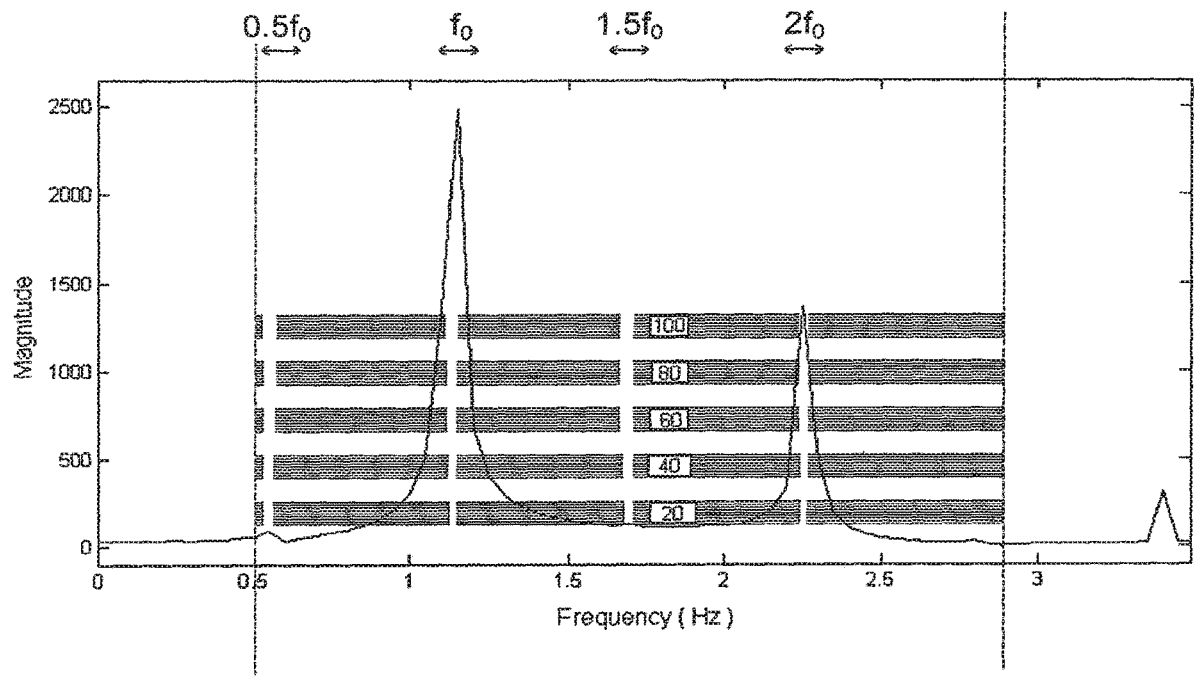
FIG. 19 is a diagram illustrating the performance of a beating detection module, for different relative magnitudes between the blood pulse and the heart pulse.

FIG. 19 is an example of frequency and amplitude ranges in which a heart pulse is detectable using the beating detection block 53. The dotted lines indicate the frequency range of a normal heart, and the dark horizontal bands indicate the frequencies at which a heart pulse could be detected in a system using a pumping frequency of 1.13 Hz. The five rows of horizontal bands represent different relative magnitudes between the blood pump and heart pulses, ranging from 20:1, 40:1, 60:1, 80:1 and 100:1 from the bottom row to the top row.

The invention has mainly been described above with reference to a few embodiments. However, as is readily appreciated by a person skilled in the art, other embodiments than the ones disclosed above are equally possible within the scope and spirit of the invention.

For example, the pressure signal may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, etc.

Further, the illustrated embodiments are applicable for surveillance of all types of extracorporeal blood flow circuits in which blood is taken from a patient's circulation to have a process applied to it before it is returned to the circulation. Such blood flow circuits include hemodialysis, hemofiltration, hemodiafiltration, plasmapheresis, apheresis, extracorporeal membrane oxygenation, assisted blood circulation, and extracorporeal liver support/dialysis.

Further, the inventive monitoring techniques are applicable to any type of pumping device that generates pressure pulses in the first fluid containing system, not only rotary peristaltic pumps as disclosed above, but also other types of positive displacement pumps, such as linear peristaltic pumps, diaphragm pumps, as well as centrifugal pumps.

Still further, the inventive monitoring techniques are applicable also for monitoring the integrity of the fluid connection between the blood vessel access and the arterial needle based on a measurement signal from one or more arterial pressure sensors. Such a monitoring technique may provide a faster detection of malfunction than the conventional air detector, and more reliable detection of malfunction than conventional comparison of average pressure levels to threshold values. In such an application, the aforesaid reference signal may be derived from one or more venous pressure sensors in the extracorporeal blood flow circuit.

Also, it is to be understood that the monitoring technique is equally applicable to single-needle dialysis.

The inventive monitoring techniques are also applicable when the measurement signal originates from a pressure sensor arranged to sense the pressure in the human blood system. In such an embodiment, the first fluid containing system (S1) is the human blood system, the second fluid containing system (S2) is the extracorporeal blood flow circuit, and the fluid connection (C) may be formed by a connection between an access device and a blood vessel access. The first pulses thus originate from the human heart, and the second pulses originate from the pumping device in the extracorporeal blood flow circuit (and/or any other pulse generator within or associated with the extracorporeal blood flow circuit), and the integrity of the fluid connection is determined by applying the first and/or second inventive concepts to detect the presence/absence of the second pulses in the measurement signal.

Figure 20:
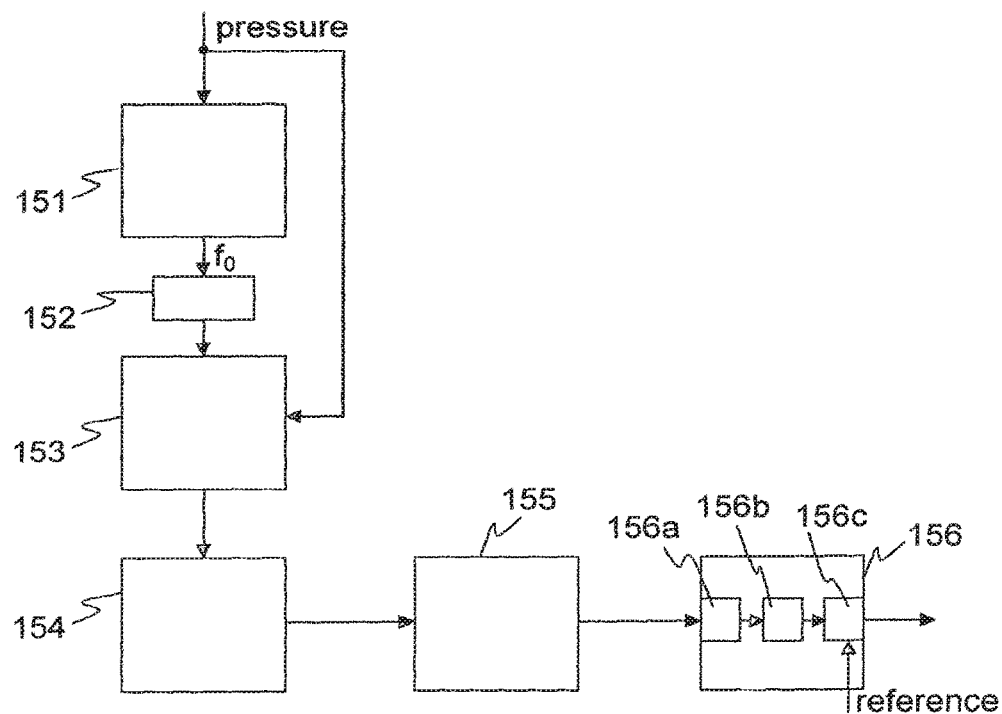
FIG. 20 is a schematic view of an arrangement of analog devices for detection of a beating component in a pressure signal.

Furthermore, the monitoring process is not limited to digital signal processing. FIG. 20 illustrates an exemplary combination of analog devices for detection of a beating component in a pressure signal. The individual devices are known per se, and alternative implementations are readily available to the skilled person. The exemplary combination of analog devices includes a bandpass filter 151 which is adapted to filter an incoming pressure signal to isolate a signal component at the base frequency (f0) of the pumping device. A frequency multiplier 152 is arranged to receive the filtered pressure signal and is controllable to generate a corresponding output signal at a selected multiple (0.5, 1, 2.5, 3 etc) of the base frequency. The output signal from the multiplier 152 is input as a control signal to a controllable bandpass filter 153, which is adapted to receive and filter the incoming pressure signal. The filter 153 is thereby controlled to process the pressure signal by removing all frequencies except for a frequency band around the frequency of the control signal from the multiplier 152 (cf. step 406 in FIG. 12). The processed pressure signal is input to a peak detector 154 which thereby generates an envelope signal, which in turn is fed to a high-pass filter 155 which removes any DC component from the envelope signal. Optionally, a low-pass filter (not shown) may be included to remove high-frequency noise from the envelope signal. Finally, the envelope signal is received by an amplitude detector 156 which is adapted to determine presence/absence of a beating signal. The amplitude detector may include, in sequence, a full wave rectifier 156a, a low-pass filter 156b and a comparator 156c which is fed with a reference signal. If the amplitude of the input signal to the comparator 156c exceeds the reference signal, the comparator 156c may output a signal indicating presence of a beating signal, otherwise not, or vice versa.

The above-described inventive concepts may also be applicable to monitoring the integrity of fluid connections for transferring other liquids than blood. Likewise, the fluid connections need not be provided in relation to a human, but could be provided in relation to any other type of fluid containing system.

In one example, the fluid connection is provided between a blood processing circuit and a container/machine, wherein blood is pumped from one container/machine through a blood processing device in the blood processing circuit and back to the container/machine, or to another container/machine downstream of the blood processing device. The blood processing device could be any known device configured to modify and/or analyse the blood.

In a further example, the fluid connection is provided between a dialyser and a reprocessing system, which reprocesses the dialyser by pumping water, optionally together with suitable chemicals through the dialyser. An example of a dialyser reprocessing system is known from US2005/0051472.

In another example, the fluid connection is provided between a dialysate supply and a dialysate regeneration system, which circulates dialysate from the dialysate supply through a dialysate regeneration device and back to the supply. An example of a dialysate regeneration device is known from WO 05/062973.

In yet another example, the fluid connection is provided in an arrangement for priming an extracorporeal blood flow circuit by pumping a priming fluid from a supply via the blood flow circuit to a dialyser. The priming fluid may e.g. be dialysis solution, saline, purified water, etc.

In a still further example, the fluid connection is provided in an arrangement for cleaning and disinfecting the dialysis solution flow path of a dialysis machine, which pumps a cleaning fluid via a flow path to a dialyser/dialyser tubing. The cleaning fluid may e.g. be hot water, a chemical solution, etc.

In a further example, the fluid connection is provided in an arrangement for purifying water, which pumps water from a supply through a purifying device. The purifying device may use any known water purification technique, e.g. reverse osmosis, deionization or carbon absorption.

In another example, the fluid connection is provided in an arrangement for providing purified water to a dialysis machine, e.g. to be used in the preparation of dialysis solution therein.

In all of these examples, and in other applications related to medical treatment of human or animal patients, it may be vital to monitor the integrity of the fluid connection. Such monitoring can be accomplished according to the inventive concepts disclosed herein.

What is claimed is:

1. A method for monitoring the integrity of a fluid connection between first and second fluid containing systems based on at least one time-dependent measurement signal from at least one pressure sensor in the first fluid containing system, wherein the first fluid containing system includes an extracorporeal blood flow circuit comprising an arterial access device, a blood processing device, a venous access device and a first pulse generator, and the second fluid containing system includes a human blood system comprising a blood vessel access and a second pulse generator, wherein:

the arterial access device is for connecting to the human blood system, the venous access device is connected to the blood vessel access to form the fluid connection, the first pulse generator includes a pumping device arranged in the extracorporeal blood flow circuit to pump blood from the arterial access device through the blood processing device to the venous access device, and the at least one pressure sensor is arranged to detect first pulses originating from the first pulse generator and second pulses originating from the second pulse generator, said method comprising:

receiving, at a processor, said at least one time-dependent measurement signal from the at least one pressure sensor;

generating, by the processor, a time-dependent monitoring signal based on said at least one-time dependent measurement signal in which the first pulses are eliminated;

calculating, by the processor, a parameter value based on signal segment profile values within a time window in the time-dependent monitoring signal, the parameter value representing a distribution of the signal segment profile values, wherein said calculating includes matching the signal segment profile values within the time window to a predicted temporal signal profile of the second pulses;

determining, by the processor, the integrity of the fluid connection based at least partly on the parameter value; and controlling blood flow through the extracorporeal blood flow circuit based at least in part on the parameter value.

2. The method of claim 1, wherein said calculating comprises:
calculating the parameter value as a statistical dispersion measure of the signal segment profile values within the time window.

3. The method of claim 2, wherein the statistical dispersion measure includes at least one of: a standard deviation, a variance, a coefficient of variation, a sum of differences, an energy, a power, a sum of absolute deviations from an average value, and an average of absolute differences from an average value.

4. The method of claim 1, wherein the parameter value is a correlation value resulting from said matching.

5. The method of claim 1, wherein said calculating comprises:
calculating a cross-correlation between the signal segment profile values within the time window and the predicted temporal signal profile; and
identifying a maximum correlation value in the cross-correlation, wherein said determining includes comparing the maximum correlation value to a threshold value.

6. The method of claim 5, wherein said calculating comprises:
obtaining a time point of the maximum correlation value, and validating the maximum correlation value by comparing the time point to a predicted time point.

7. The method of claim 1, further comprising the steps of (i) obtaining a reference pressure signal from a reference sensor in the first fluid containing system, wherein the reference sensor is arranged to detect said second pulses even if the fluid connection is compromised, and (ii) calculating the predicted temporal signal profile based on the reference pressure signal.

8. The method of claim 7, further comprising the steps of calculating a magnitude value indicative of a magnitude of the second pulses in the reference pressure signal, and comparing the magnitude value to a limit, wherein the step of calculating the predicted temporal signal profile based on the reference pressure signal is conditioned upon said comparing of the magnitude value to the limit.

9. The method of claim 7, wherein the step of calculating the predicted temporal signal profile comprises adjusting for a difference in transit time between the reference sensor and said at least one pressure sensor.

10. The method of claim 9, wherein said difference in transit time is given by a predefined value.

11. The method of claim 9, wherein said difference in transit time is calculated based on a difference in fluid pressure between a location of the reference sensor and said at least one pressure sensor.

12. The method of claim 1, wherein the time window is selected so as to contain at least one second pulse originating from the second pulse generator.

13. The method of claim 12, wherein the length of the time window is chosen to exceed a maximum pulse repetition interval of the second pulse generator.

14. The method of claim 12, wherein the time window is chosen based on timing information indicative of the timing of the second pulses in said at least one time-dependent measurement signal.

15. The method of claim 14, wherein the timing information is obtained from a pulse sensor coupled to the second fluid containing system.

16. The method of claim 14, wherein the timing information is based on a relative timing of previously detected second pulses in the time-dependent measurement signal.

17. The method of claim 14, wherein the at least one time dependent measurement signal comprises at least one venous measurement signal derived from at least one venous pressure sensor located downstream of the pumping device, and at least one arterial measurement signal derived from at least one arterial pressure sensor located upstream of the pumping device, and wherein the monitoring signal is generated based on said at least one venous measurement signal, said method comprising:
identifying at least one second pulse originating from the second pulse generator in said at least one arterial measurement signal; and
calculating the timing information from the at least one identified second pulse.

18. The method of claim 14, further comprising:
intermittently turning off the first pulse generator;
identifying at least one second pulse originating from the second pulse generator in said at least one time-dependent measurement signal; and
calculating the timing information from the identified second pulse.

19. The method of claim 14, further comprising:
identifying a set of candidate second pulses based on said at least one time-dependent measurement signal;
deriving a sequence of candidate time points based on the set of candidate second pulses;
validating the sequence of candidate time points against a temporal criterion; and
calculating the timing information as a function of the validated sequence of candidate time points.

20. The method of claim 1, wherein said calculating comprises:
identifying a candidate second pulse in the monitoring signal and a corresponding candidate time point; and
validating the candidate second pulse based on the candidate time point in relation to timing information indicative of the timing of the second pulses in said at least one time-dependent measurement signal.

21. A non-transitory computer readable storage medium comprising instructions for causing a computer to perform the method of claim 1.

22. A device for monitoring the integrity of a fluid connection between an extracorporeal blood flow circuit and a human blood system wherein the extracorporeal blood flow circuit comprises an arterial access device connecting to the human blood system, a blood processing device, a venous access device, and a first pulse generator, and the human blood system comprises a blood vessel access and a second pulse generator, wherein:
the venous access device is configured to be connected to the blood vessel access to form the fluid connection,
the first pulse generator includes a pumping device configured to be arranged in the extracorporeal blood flow circuit to pump blood from the arterial access device through the blood processing device to the venous access device, and
at least one pressure sensor is configured to detect first pulses originating from the first pulse generator and second pulses originating from the second pulse generator,
said device comprising:
an input for at least one time-dependent measurement signal from the at least one pressure sensor in the extracorporeal blood flow circuit; and
a signal processor connected to said input, said signal processor comprising a processing module configured to (i) generate, based on said at least one time-dependent measurement signal, a time-dependent monitoring signal in which the first pulses are eliminated, (ii) calculate a parameter value based on signal segment profile values within a time window in the monitoring signal, the parameter value representing a distribution of the signal segment profile values, wherein said calculation includes matching the signal segment profile values within the time window to a predicted temporal signal profile of the second pulses, said signal processor being configured to determine the integrity of the fluid connection based at least partly on the parameter value, and (iii) control blood flow through the extracorporeal blood flow circuit based at least in part on the parameter value.

23. A device for monitoring the integrity of a fluid connection between an extracorporeal blood flow circuit and a human blood system, wherein the extracorporeal blood flow circuit comprises an arterial access device connecting to the human blood system, a blood processing device, a venous access device, and a first pulse generator, and the human blood system comprises a blood vessel access and a second pulse generator, wherein:
the venous access device is configured to be connected to the blood vessel access to form the fluid connection,
the first pulse generator includes a pumping device configured to be arranged in the extracorporeal blood flow circuit to pump blood from the arterial access device through the blood processing device to the venous access device, and
at least one pressure sensor is configured to detect first pulses originating from the first pulse generator and second pulses originating from the second pulse generator,
said device comprising:
means for receiving said at least one time dependent measurement signal;
means for generating, based on said at least one time-dependent measurement signal, a time-dependent monitoring signal in which the first pulses are eliminated;
means for repeatedly calculating a parameter value based on signal segment profile values within a plurality of time windows in the monitoring signal, the parameter value representing a distribution of the signal segment profile values, wherein said calculating includes matching the signal segment profile values within each of the plurality of time windows to a predicted temporal signal profile of the second pulses;
means for determining the integrity of the fluid connection based at least partly on each repeatedly calculated parameter value; and
means for controlling blood flow through the extracorporeal blood flow circuit based at least in part on each repeatedly calculated parameter value.

* * * * *